(12) United States Patent
Edmunds et al.

(10) Patent No.: US 10,435,401 B2
(45) Date of Patent: Oct. 8, 2019

(54) PESTICIDALLY ACTIVE TETRACYCLIC DERIVATIVES WITH SULPHUR CONTAINING SUBSTITUENTS

(71) Applicant: Syngenta Participations AG, Basel (CH)

(72) Inventors: Andrew Edmunds, Stein (CH); Michel Muehlebach, Stein (CH); Pierre Joseph Marcel Jung, Stein (CH); Andre Jeanguenat, Stein (CH); Anke Buchholz, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/510,064

(22) PCT Filed: Sep. 9, 2015

(86) PCT No.: PCT/EP2015/070537
§ 371 (c)(1),
(2) Date: Mar. 9, 2017

(87) PCT Pub. No.: WO2016/041819
PCT Pub. Date: Mar. 24, 2016

(65) Prior Publication Data
US 2017/0260182 A1    Sep. 14, 2017

(30) Foreign Application Priority Data

Sep. 16, 2014   (EP) ...................... 14184887

(51) Int. Cl.
*C07D 471/04* (2006.01)
*A01N 25/08* (2006.01)
*A01N 43/50* (2006.01)

(52) U.S. Cl.
CPC ........... *C07D 471/04* (2013.01); *A01N 25/08* (2013.01); *A01N 43/50* (2013.01)

(58) Field of Classification Search
CPC .................................................. C07D 471/04
USPC .......................................... 546/118; 514/303
See application file for complete search history.

(56) References Cited

U.S. PATENT DOCUMENTS 9,018,134 B2 * 4/2015 Takahashi .............. A01N 43/76
    504/246
2014/0194290 A1    7/2014 Takahashi et al.

FOREIGN PATENT DOCUMENTS

| JP | 2008308448 A | 12/2008 |
| WO | 2011090127 A1 | 7/2011 |
| WO | 2012/086848 A1 | 6/2012 |
| WO | 2013187423 A1 | 12/2013 |
| WO | 2013191113 A1 | 12/2013 |

OTHER PUBLICATIONS

European Search Report for 14184887.9, dated Jan. 13, 2015.
Sluka J et al: "2-Phenylbenzimidazoles as Potential Anthelminthics", COLL CZECH CHEM COMM, 41, Jan. 1, 1976, pp. 3628-3631, XP009156807.
International Search Report & Written Opinion for PCT/EP2015/070537.

* cited by examiner

*Primary Examiner* — Patricia L Morris
(74) *Attorney, Agent, or Firm* — Baker & Hostetler, LLP; Toni-Junell Herbert

(57) ABSTRACT

Compounds of formula (I) wherein the substituents are as defined in claim 1, and the agrochemically acceptable salts salts, stereoisomers, enantiomers, tautomers and N-oxides of those compounds, can be used as insecticides and can be prepared in a manner known per se.

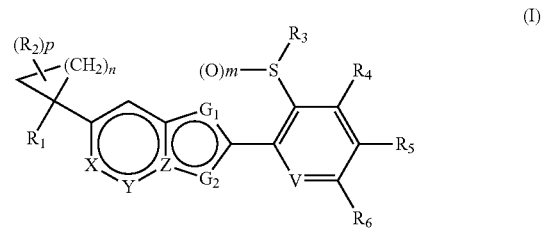

18 Claims, No Drawings

PESTICIDALLY ACTIVE TETRACYCLIC DERIVATIVES WITH SULPHUR CONTAINING SUBSTITUENTS

RELATED APPLICATION INFORMATION

This application is a 371 of International Application No. PCT/EP2015/070537, filed 9 Sep. 2015, which claims priority to EP 14184887.9, filed 16 Sep. 2014, the contents of which are incorporated herein by reference herein.

The present invention relates to insecticidally active tetracyclic derivatives containing sulphur substituents, to compositions comprising those compounds, and to their use for controlling animal pests (including arthropods and in particular insects or representatives of the order Acarina).

Sulphur containing heterocyclic compounds with pesticidal action are known and described, for example, in WO 2013/018928, WO 2013/187423 and WO 2012/086848.

There have now been found novel sulphur containing heterocyclic derivatives with pesticidal properties.

The present invention accordingly relates to compounds of formula (I),

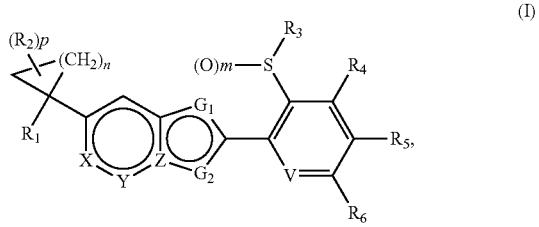

wherein
$R_1$ and $R_2$ are, independently from each other, hydrogen, $C_1$-$C_6$alkyl, $C_1$-$C_6$haloalkyl, cyano, nitro, C(O)$R_8$, C(O)OR$_9$, CONR$_{10}$R$_{11}$, or S(O)$_{m_1}$R$_{12}$;
$R_3$ is $C_1$-$C_3$alkyl, $C_1$-$C_3$haloalkyl, $C_3$-$C_6$halocycloalkyl, $C_3$-$C_6$cycloalkyl-$C_1$-$C_4$alkyl, $C_3$-$C_6$cycloalkyl or $C_3$-$C_6$halocycloalkyl-$C_1$-$C_4$alkyl;
$R_4$ and $R_6$ are hydrogen, halogen, or $C_1$-$C_3$alkyl;
$R_5$ is hydrogen, halogen, cyano, nitro, $C_1$-$C_4$alkoxy, $C_1$-$C_4$alkyl, or $C_1$-$C_4$alkyl mono- or polysubstituted by substituents selected from the group consisting of halogen, hydroxy, $C_1$-$C_4$haloalkoxy, $C_1$-$C_4$alkoxy and cyano; or is $C_3$-$C_6$cycloalkyl, or $C_3$-$C_6$cycloalkyl mono- or polysubstituted by substituents selected from the group consisting of $C_1$-$C_4$alkyl, and halogen; or
$R_5$ is $C_2$-$C_6$alkenyl, $C_2$-$C_6$haloalkenyl, $C_2$-$C_6$alkynyl, $C_2$-$C_6$haloalkynyl; or
$R_5$ is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
$R_5$ is $C_1$-$C_4$haloalkylsulfanyl, $C_1$-$C_4$haloalkylsulfinyl, $C_1$-$C_4$haloalkylsulfonyl, pentafluorosulfanyl, $C_1$-$C_4$haloalkoxy, —C(O)$C_1$-$C_4$alkyl, $C_1$-$C_4$alkylsulfanyl, $C_1$-$C_4$alkylsulfinyl, or $C_1$-$C_4$alkylsulfonyl; or
$R_5$ is pyrimidine or pyridine which both can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, and —C(O)$C_1$-$C_4$alkyl;
X is nitrogen or CR$_{13}$;
Y is nitrogen or CR$_{14}$;
$G_1$ is nitrogen or CR$_{15}$;
V is nitrogen or CH;
Z is nitrogen and $G_2$ is nitrogen or CR$_{16}$; or
Z is carbon and $G_2$ is N—R$_7$, sulphur, oxygen or CR$_{16}$;
$R_7$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl;
$R_8$, $R_9$, $R_{10}$, $R_{11}$ and $R_{12}$ independently of one another are hydrogen, $C_1$-$C_6$alkyl, $C_1$-$C_6$haloalkyl, $C_3$-$C_6$cycloalkyl, $C_3$-$C_6$halocycloalkyl or $C_1$-$C_6$alkoxy-$C_1$-$C_6$alkyl, with the proviso that when $m_1$ is 2, $R_{12}$ is different from hydrogen;
$R_{13}$, $R_{14}$, $R_{15}$ and $R_{16}$ are, independently from each other, hydrogen, halogen, $C_1$-$C_4$alkyl, $C_1$-$C_4$haloalkyl, $C_1$-$C_4$haloalkyl substituted by one or more methoxy groups, or $R_{13}$, $R_{14}$, $R_{15}$ and $R_{16}$ are, independently from each other, $C_1$-$C_4$haloalkylsulfanyl, $C_1$-$C_4$haloalkylsulfinyl, $C_1$-$C_4$haloalkylsulfonyl, $C_1$-$C_4$haloalkoxy, phenylcarbonylsulfanyl, cyano, mercapto, or $C_1$-$C_4$alkoxycarbonyl;
n is 1 or 2;
m is 0, 1 or 2;
$m_1$ is 0, 1 or 2;
p is 1, 2, 3 or 4;
and agrochemically acceptable salts and N-oxides of those compounds.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl and hexyl. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl, in particular trifluoromethyl.

Alkoxy groups preferably have a chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy. Alkoxyalkyl groups have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylsulfanyl, phenylalkyl, phenoxyalkyl, may be substituted. In this case, the substituents can be in ortho, meta and/or para position. The preferred substituent positions are the ortho and para positions to the ring attachment point.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, di- or tri-substituted.

The group $(O)_m$—S can, depending on the meaning of m, represent a sulfanyl, sulfinyl or sulfonyl group.

The substituent $R_2$ can be located at every chemically possible position of the cycloalkyl ring. Therefore, the group $(CH_2)_n$ can also represent —$(CHR_2)$—, —$(C(R_2)R_2)$—, or —$(CH_2$—$C(R_2)H)$—.

Compounds of formula (I) which have at least one basic centre can form, for example, acid addition salts, for example with strong inorganic acids such as mineral acids, for example perchloric acid, sulphuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulphonic acids, such as $C_1$-$C_4$alkane- or arylsulphonic acids which are unsubstituted or substituted, for example by halogen, for example methane- or p-toluenesulphonic acid. Compounds of formula (I) which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent.

Salts of compounds of formula (I) can be converted in the customary manner into the free compounds (I), acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

A preferred group of compounds of formula (I) is represented by the compounds of formula (Ia)

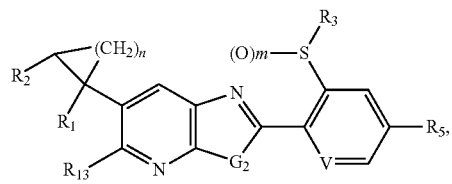

(Ia)

wherein;
$R_1$, $R_2$, $R_3$, $R_5$, $R_{13}$, V, n, and m are as defined in formula (I) above, and $G_2$ is oxygen, sulphur or is nitrogen substituted with hydrogen or with $C_1$-$C_2$alkyl. Preferred compounds of formula (Ia) are those, wherein
n is 1 or 2.

Especially preferred compounds of formula (Ia) are those, in which
$R_1$ is hydrogen, trifluoromethyl or cyano;
$R_2$ is hydrogen or cyano;
$R_3$ is $C_1$-$C_3$alkyl, $C_3$-$C_4$cycloalkyl or $C_3$-$C_4$cycloalkyl-$C_1$-$C_4$alkyl;
$R_5$ is hydrogen, $C_1$-$C_6$-haloalkyl, halogen, phenyl which can be mono- or di-substituted by substituents selected from $C_1$-$C_4$-haloalkyl or halogen, or is pyridyl which can be mono- or di-substituted by substituents selected from $C_1$-$C_4$-haloalkyl or halogen; in particular
$R_5$ is hydrogen, trifluoromethyl, halogen, 4-(trifluoromethyl)-phenyl, 5-(trifluoromethyl)-2-pyridyl, 4-chloro-phenyl, or 5-chloro-2-pyridyl.

Preferably in formula (Ia) $G_2$ is nitrogen substituted with $C_1$-$C_2$alkyl. Preferred compounds are also those, in which $R_{13}$ is hydrogen, 4-(trifluoromethyl)-2-pyridyl, 5-(trifluoromethyl)-3-pyridyl, or 2-(trifluoromethyl)-4-pyridyl. Most preferred compounds are those, wherein $R_{13}$ is hydrogen.

Preferably in formula (Ia), V is nitrogen and m is 2.

Even more highly preferred compounds of formula (Ia) are those, in which n is 1 or 2, and $R_1$ is cyano;

A further preferred group of compounds of formula (Ia) are those, in which n is 1 or 2, and $R_1$ is trifluoromethyl.

Another set of preferred compounds of formula (Ia) are those, in which V is CH.

A further preferred group of compounds of formula (Ia) are those, in which $R_1$ is hydrogen and $R_2$ is cyano.

A further preferred group of compounds of formula (I) is represented by the compounds of formula (Ib)

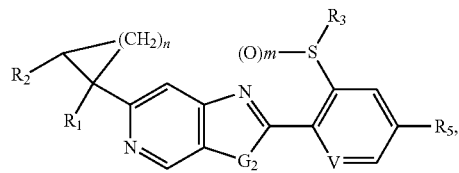

(Ib)

wherein
$R_1$, $R_2$, $R_3$, $R_5$, V, n, and m are as defined in formula (I) above, and $G_2$ is oxygen, sulphur or nitrogen substituted with hydrogen or with $C_1$-$C_2$alkyl. Preferred compounds of formula (Ib) are those, wherein n is 1 or 2.

Especially preferred compounds of formula (Ib) are those, in which
$R_1$ is hydrogen, trifluoromethyl or cyano;
$R_2$ is hydrogen or cyano;

$R_3$ is $C_1$-$C_3$alkyl, $C_3$-$C_4$cycloalkyl or $C_3$-$C_4$cycloalkyl-$C_1$-$C_4$alkyl;

$R_5$ is hydrogen, $C_1$-$C_6$-haloalkyl, halogen, phenyl which can be mono- or di-substituted by substituents selected from $C_1$-$C_4$-haloalkyl or halogen, or is pyridyl which can be mono- or di-substituted by substituents selected from $C_1$-$C_4$-haloalkyl or halogen; in particular $R_5$ is hydrogen, trifluoromethyl, halogen, 4-(trifluoromethyl)-phenyl, 5-(trifluoromethyl)-2-pyridyl, 4-chloro-phenyl, or 5-chloro-2-pyridyl.

Preferably in formula (Ib) $G_2$ is nitrogen substituted with $C_1$-$C_2$alkyl.

Preferably in formula (Ib), V is nitrogen and m is 2.

Even more highly preferred compounds of formula (Ib) are those, in which n is 1 or 2, and $R_1$ is cyano;

A further preferred group of compounds of formula (Ib) are those, in which n is 1 or 2, and $R_1$ is trifluoromethyl.

Another set of preferred compounds of formula (Ib) are those, in which V is CH.

A further preferred group of compounds of formula (Ib) are those, in which $R_1$ is hydrogen and $R_2$ is cyano.

A further preferred group of compounds of formula (I) is represented by the compounds of formula (Ic)

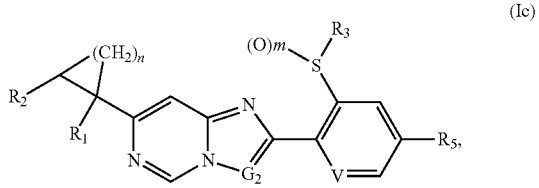

(Ic)

wherein $R_1$, $R_2$, $R_3$, $R_5$, V, n, and m are as defined in formula (I) above, $G_2$ is nitrogen or $G_2$ is methine or CH—$CH_3$.

Preferred compounds of formula (Ic) are those wherein n is 1, or 2;

$R_1$ hydrogen, cyano or trifluoromethyl;

$R_2$ is hydrogen or cyano;

$R_3$ is $C_1$-$C_3$alkyl, $C_3$-$C_4$cycloalkyl or $C_3$-$C_4$cycloalkyl-$C_1$-$C_4$alkyl;

$R_5$ is hydrogen, $C_1$-$C_6$-haloalkyl, halogen, phenyl which can be mono- or di-substituted by substituents selected from $C_1$-$C_4$-haloalkyl or halogen, or is pyridyl which can be mono- or di-substituted by substituents selected from $C_1$-$C_4$-haloalkyl or halogen; in particular $R_5$ is hydrogen, trifluoromethyl, halogen, 4-(trifluoromethyl)-phenyl, 5-(trifluoromethyl)-2-pyridyl, 4-chloro-phenyl, or 5-chloro-2-pyridyl.

Preferably in the compounds of formula (Ic), $R_2$ hydrogen and $R_1$ is cyano.

In a further preferred group of compounds of formula (Ic) $R_1$ is trifluoromethyl.

In another further preferred group of compounds of formula (Ic) $G_2$ is nitrogen.

A further preferred group are those compounds of formula (Ic), wherein $G_2$ is methine.

Preferred are also compounds of formula (Ic), V is nitrogen and m is 2.

Further preferred compounds of formula (Ic) are those, in which V is CH.

A further preferred group of compounds of formula I is represented by the compounds of formula (Id)

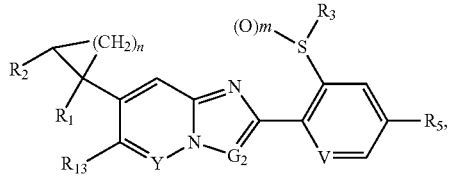

(Id)

wherein $R_1$, $R_2$, $R_3$, $R_5$, $R_{12}$, V, Y, n and m are as defined in formula (I) above, $G_2$ is nitrogen or $G_2$ is methine or CH—$CH_3$.

Preferred compounds of formula (Id) are those wherein n is 1, or 2;

$R_1$ hydrogen, cyano or trifluoromethyl;

$R_2$ Is hydrogen or cyano;

$R_3$ is $C_1$-$C_3$alkyl, $C_3$-$C_4$cycloalkyl or $C_3$-$C_4$cycloalkyl-$C_1$-$C_4$alkyl;

$R_5$ is hydrogen, $C_1$-$C_6$-haloalkyl, halogen, phenyl which can be mono- or di-substituted by substituents selected from $C_1$-$C_4$-haloalkyl or halogen, or is pyridyl which can be mono- or di-substituted by substituents selected from $C_1$-$C_4$-haloalkyl or halogen; in particular $R_5$ is hydrogen, trifluoromethyl, halogen, 4-(trifluoromethyl)-phenyl, 5-(trifluoromethyl)-2-pyridyl, 4-chloro-phenyl, or 5-chloro-2-pyridyl.

Preferred compounds of formula (Id) are those, in which $R_{13}$ is hydrogen, 4-(trifluoromethyl)-2-pyridyl, 5-(trifluoromethyl)-3-pyridyl, or 2-(trifluoromethyl)-4-pyridyl. Most preferred compounds of formula (Id) are those, wherein $R_{13}$ is hydrogen.

Especially preferred compounds of formula (Id) are those, in which $R_2$ is hydrogen and $R_1$ is cyano. In a further preferred group of compounds of formula (Id) $R_1$ is trifluoromethyl.

In a more preferred group of compounds of formula (Id), $G_2$ is nitrogen or methine and Y is nitrogen or methine. Especially preferred compounds of formula (Id) are those, wherein $G_2$ is methine.

In a highly preferred group of compounds of formula (Id), V is nitrogen and m is 2.

In another set of preferred compounds of formula (Id) V is CH.

In an especially preferred embodiment of the compounds of formula I, $R_1$ is hydrogen or cyano;
$R_2$ is hydrogen;
$R_3$ is $C_1$-$C_4$alkyl;
$R_4$ is hydrogen;
$R_5$ is $C_1$-$C_4$haloalkyl;
$R_6$ is hydrogen;
p is 1;
n is 1 or 2;
m is 0 or 2; preferably 2;
X is CH;
Y is N;
Z is carbon;
$G_1$ is N;
$G_2$ is N—$R_7$;
$R_7$ is $C_1$-$C_4$alkyl; and
V is N.

The process according to the invention for preparing compounds of formula (I) is carried out in principle by methods known to those skilled in the art. More specifically, compounds of formula (I), wherein $R_1$ is cyano may be prepared by transition-metal-catalyzed coupling of a compound of formula (II)

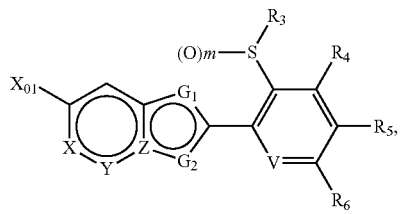
(II)

wherein X, Y, Z, $G_1$, $G_2$, $R_3$, $R_4$ $R_5$, $R_6$, m and V are described under formula (I) above, and $X_{01}$ is a halogen or a triflate group with an acetonitrile anion equivalent, to give compounds of formula (III).

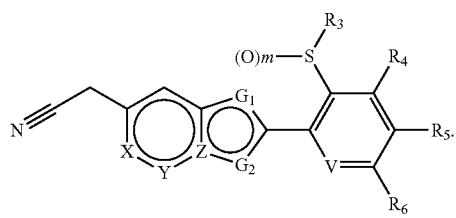
(III)

A variety of acetonitrile anion equivalents can be used in such reactions. Examples of such are tri-n-butylstannylacetonitrile, which can be coupled to compounds of formula (II) under Stille reaction conditions as described by Mitiga et. al. (*Chem. Lett.* 1984, 1511), or trimethylsilylacetonitrile in the presence of a palladium catalyst, such as tris(dibenzylideneacetone)dipalladium(0), and a ligand, for example Xantphos or P(t-Bu)3, a fluoride source, for example $ZnF_2$, in an dipolar aprotic solvent such as DMF, at temperatures between 80-120° C. Such reactions are well precedented in the literature, for example see Hartwig et. al. (*J. Am. Chem. Soc.* 2002, 124, 9330, and *J. Am. Chem. Soc.* 2005, 127, 15824).

Alternatively compounds of formula (III) can be prepared by a Suzuki reaction of a compound of formula (II) with a boronic acid of formula (IV);

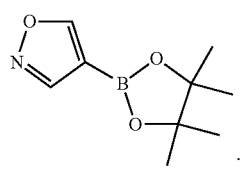
(IV)

In the presence of a base, such as potassium fluoride or cesium carbonate, a palladium catalysts, such as [1,1'-Bis (diphenylphosphino) ferrocene]dichloropalladium(II), and a polar aprotic solvent such as DMSO or DMF, at temperatures between 80-150° C. The reaction to compounds of formula (II) proceeds through an intermediate of formula (V)

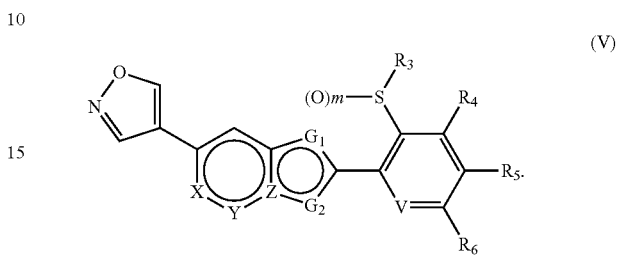
(V)

The intermediate (V) can be converted directly to compounds of formula (III) in one pot, or isolated, and converted in a separate step to compounds of formula (III) by treatment with a suitable base, for example potassium fluoride or cesium carbonate. Such reactions are well known in the literature and have been described in *J. Am. Chem. Soc.* 2011, 133, 6948-6951.

Treatment of compounds of formula (III) in the presence of a base, such as sodium hydride, in an inert solvent such as DMF, or cesium carbonate in an aprotic solvent such as acetone or acetonitrile, in the presence of a compound of formula (VI), wherein $R_2$, p, and n are as defined previously and $X_{02}$ is leaving group such as halogen or triflate;

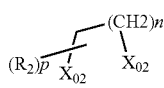
(VI)

To give compounds of formula ($Ia_{01}$)

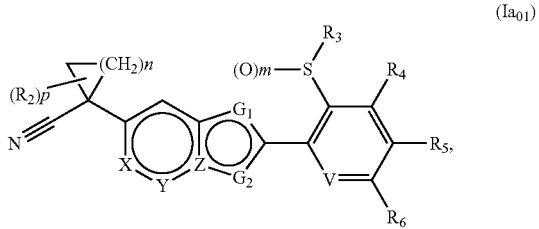
($Ia_{01}$)

wherein $R_2$, p, n, m, $R_3$, $R_4$, $R_5$, $R_6$, X, Y, Z, V, $G_1$, and $G_2$ are as described in formula (I). The chemistry is summarized in scheme 1.

Scheme 1
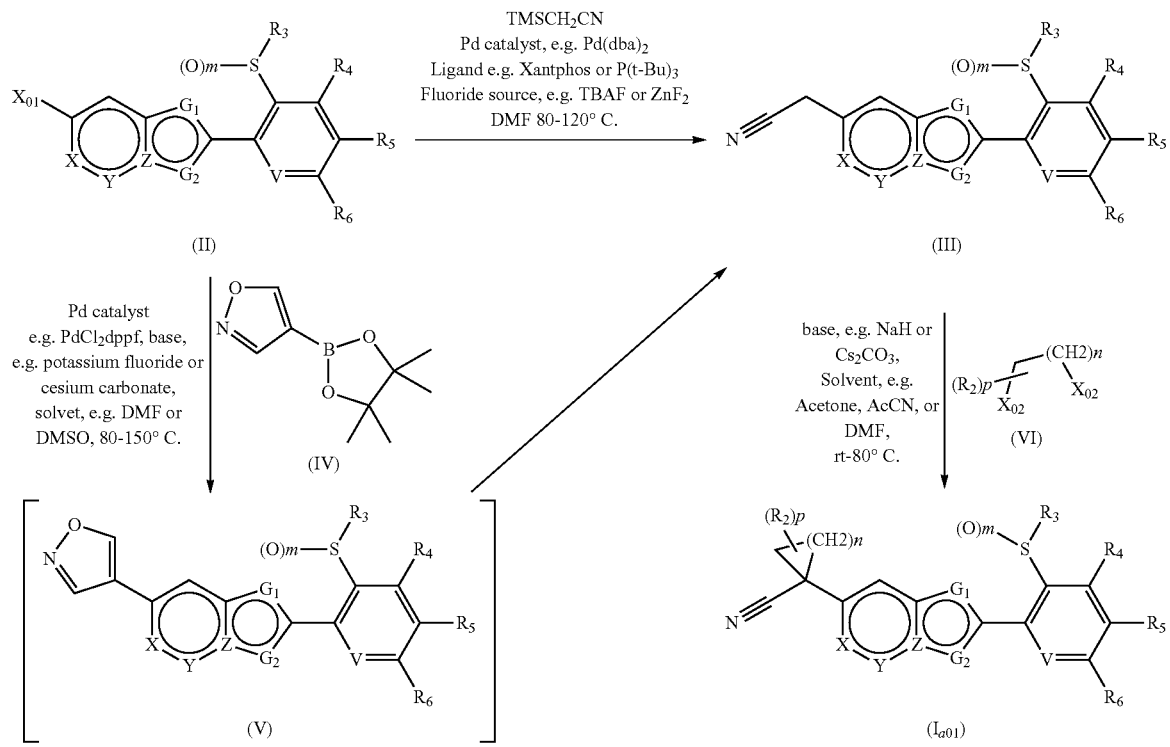
Compounds of formula (I$_{a01}$) can be converted to compounds of formula (I) wherein R$_1$ is C(O)R$_8$, C(O)OR$_9$, CONR$_{10}$R$_{11}$ by methods known to those skilled in the art, and illustrated in scheme 2.

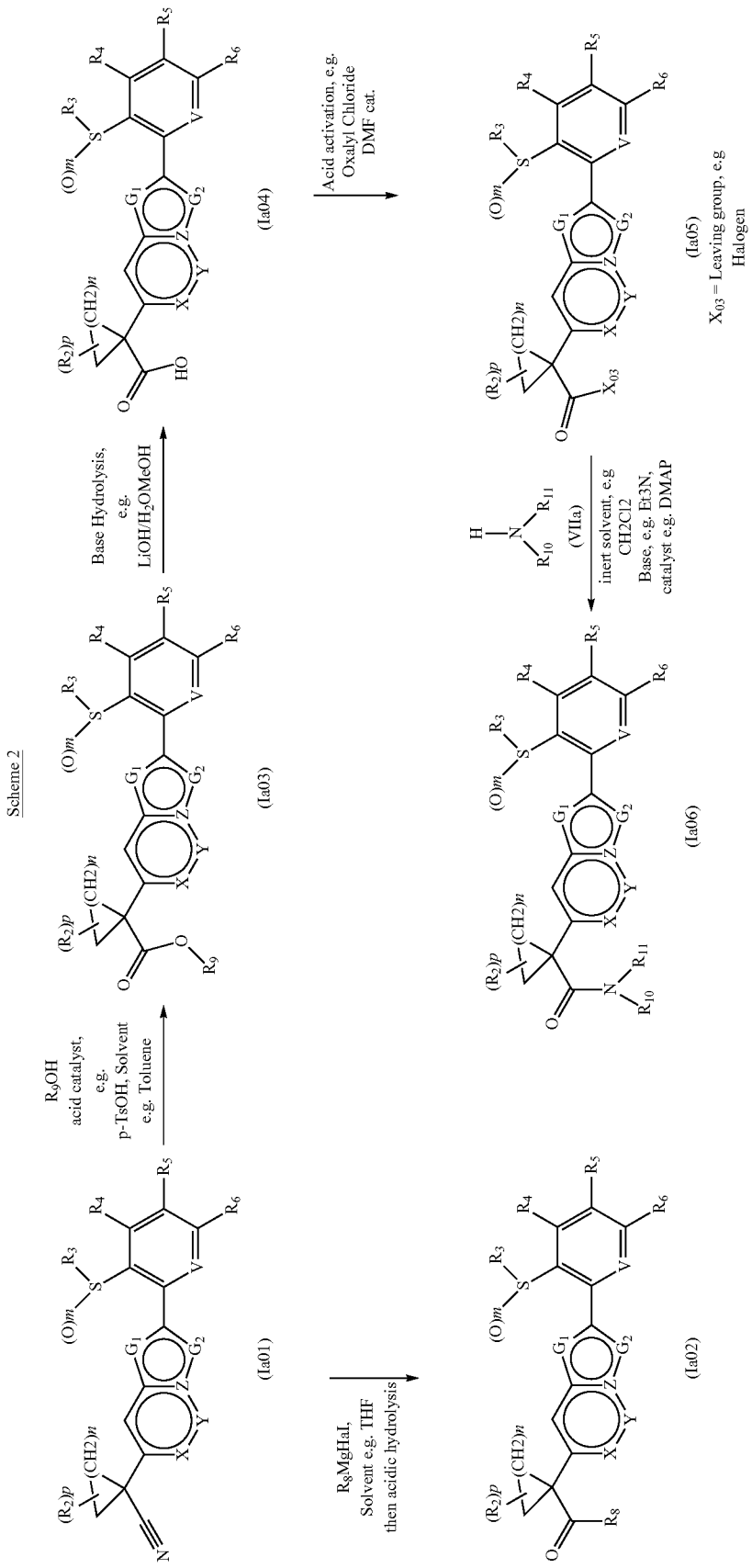

In scheme 2, compounds of formula ($Ia_{01}$) wherein $R_2$, p, n, m, $R_3$, $R_4$, $R_5$, $R_6$, X, Y, Z, V, $G_1$, and $G_2$ are as described in formula (I) can be treated with a Grignard reagent of formula $R_8MgHal$, followed by acidic hydrolysis (as described in C. Ferri, "Reaktionen der Organischen Synthese", Georg Thieme Verlag, Stuttgart, 1978, page 324ff.) to give compounds of formula ($Ia_{02}$), and wherein $R_8$ is as defined in formula (I). Compounds of formula ($Ia_{03}$) can be readily hydrolysed to the corresponding acid of formula ($Ia_{04}$) by methods to known to those skilled in the art, for example by treatment with an alkaline base, for example lithium hydroxide, in water and a water miscible solvent, for example methanol or acetone. Compounds of ($Ia_{04}$) can be activated to compounds of formula ($Ia_{05}$), wherein ($X_{03}$) is a leaving group such as halogen, or a mixed anhydride by methods known to those skilled in the art and described for example in *Chem. Soc. Rev.,* 2009, 38, 606-631. Subsequent treatment of compounds of formula ($Ia_{05}$) with compounds of formula (VIIa) in the presence of a base, for example triethyl amine, and a catalyst, for example DMAP in an inert solvent, for example methylene chloride, leads to compounds of formula ($Ia_{06}$).

Alternatively, compounds of formula (III) can be obtained from compounds of formula (II) by insertion of zinc into the C—$X_{01}$ bond, for example by treatment with activated zinc metal in an an inert solvent, such as THF or diethyl ether, or by transmetallation of the corresponding lithium or magnesium reagents. The preparation of organo zinc reagents from halogens is well known to those skilled in the art and has been described in for example by Knochel et. al. in *Chem. Rev.* 1993, 93, 2117. Subsequent reaction of the organozinc reagent with a compound of of formula (VII)

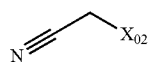

(VII)

wherein $X_{02}$ is halogen, preferably bromine, in the presence of a catalyst, for example Ni(acac)$_2$, and a phosphine ligand, for example cyclohexyldiphenylphosphine, in an inert solvent such as tetrahydrofurane leads to compounds of formula (III). Such chemistry has been described in the literature (see *Synthesis,* 1987, 40-42). The compounds of formula (III) are converted to compounds of formula (I) as described in schemes 1 and 2.

Compounds of formula (I) wherein $R_1$ is H can be prepared by direct Suzuki coupling coupling of compounds of formula (II) with Boronic acids of formula (VIIa) or Mollander salts of formula (VIIIb) by methods known to those skilled in the art, and described for example in *Tetrahedron Letters,* 43, 6987, 2002 or WO 2014/025736.

Scheme 3:

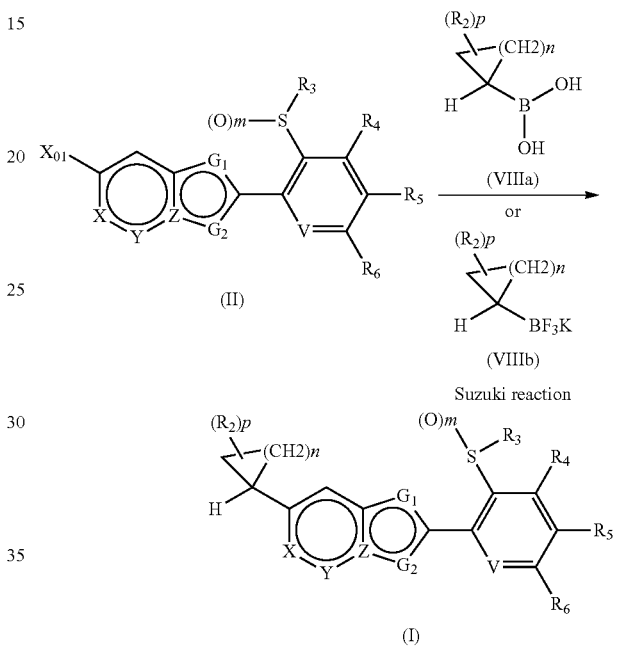

A further approach to compounds of formula (I) is illustrated in scheme 4.

Scheme 4:

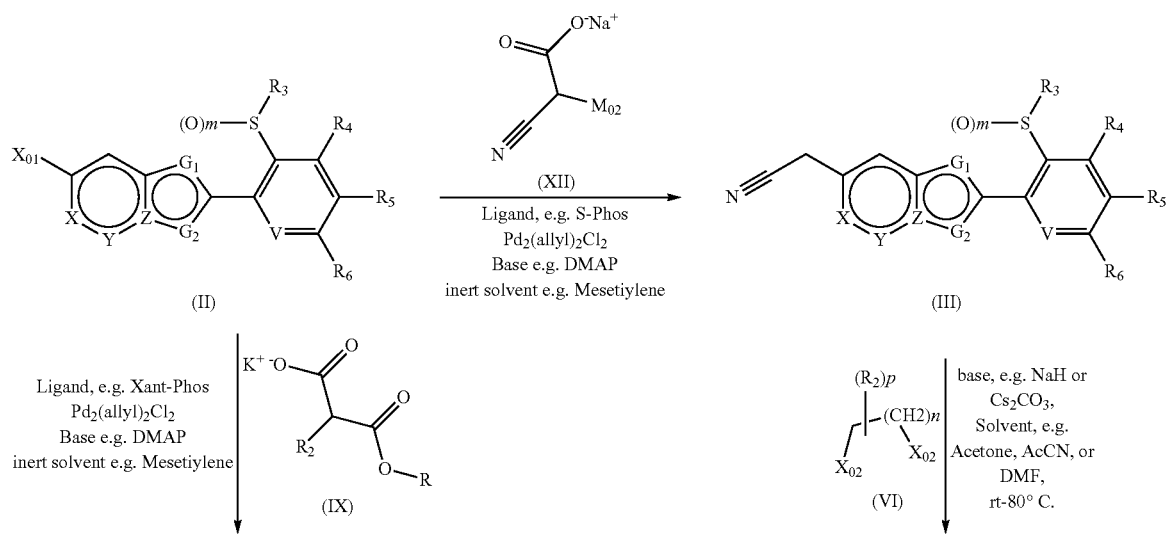

-continued

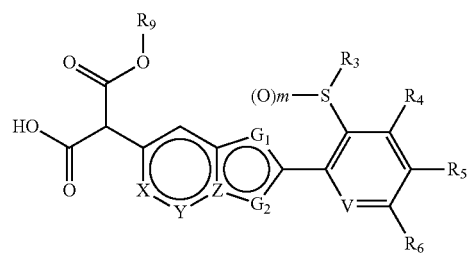

(X)

Decarboxylation or by heating in e.g. DMSO at tempertaures between 70-140 deg.

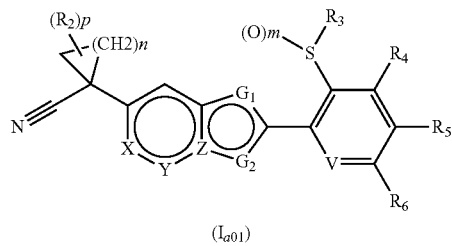

(I_{a01})

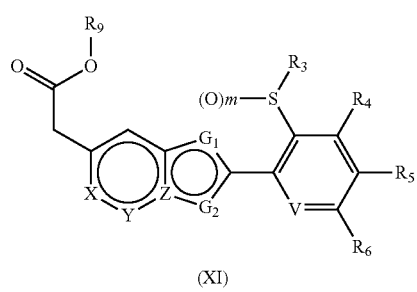

(XI)

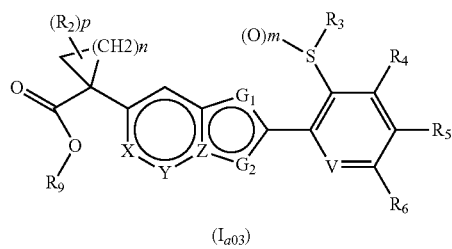

(I_{a03})

(VI)
base, e.g. NaH or Cs$_2$CO$_3$,
Solvent, e.g. Acetone, AcCN, or DMF,
rt-80° C.

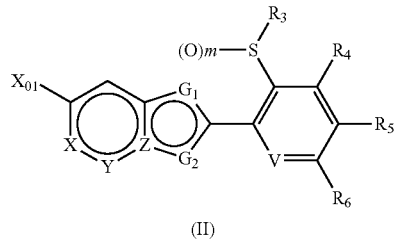

(II)

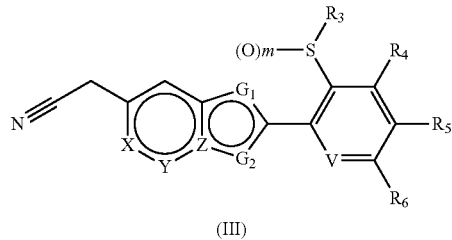

(III)

(XII)
Ligand, e.g. S-Phos
Pd$_2$(allyl)$_2$Cl$_2$
Base e.g. DMAP
inert solvent e.g. Mesetiylene Ligand, e.g. Xant-Phos
Pd$_2$(allyl)$_2$Cl$_2$
Base e.g. DMAP
inert solvent e.g. Mesetiylene

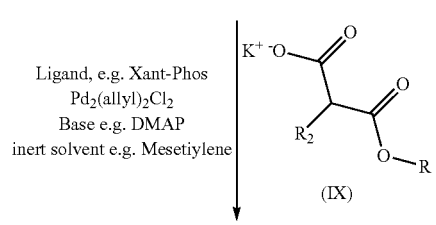

(IX)

base, e.g. NaH or Cs$_2$CO$_3$,
Solvent, e.g. Acetone, AcCN, or DMF,
rt-80° C.

(VI)

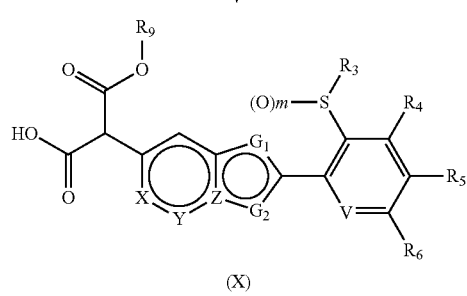

(X)

Decarboxylation or by heating in e.g. DMSO at tempertaures between 70-140 deg.

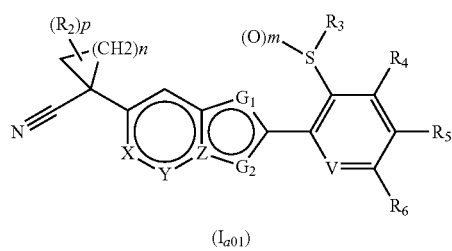

(I_{a01})

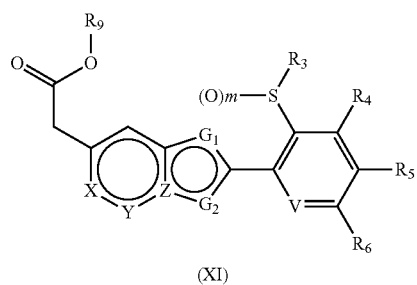
(XI)

-continued

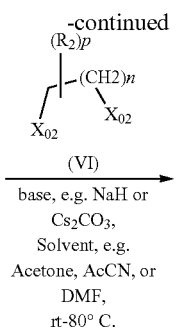
(VI)

base, e.g. NaH or Cs₂CO₃,
Solvent, e.g.
Acetone, AcCN, or
DMF,
rt-80° C.

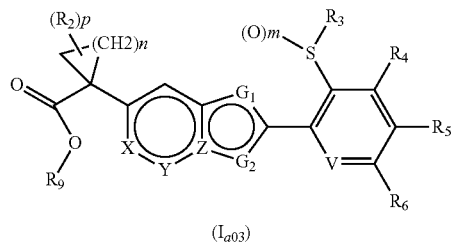
($I_{a03}$)

As shown in scheme 4, compound of formula (II) is cross-coupled with a compound of formula (IX) in the presence of Ligand, e.g. Xant-Phos, a suitable palladium catalyst, e.g. Pd₂(allyl)₂Cl₂, and a base e.g. DMAP inert solvent e.g. mesitylene as described in e.g. Y. S. Feng et al. Tetrahedron, 2012, 68, 2113, to give a compound of formula (X) wherein $G_1$, $G_2$, $R_3$, $R_4$, $R_5$, $R_6$, $R_9$, m, V, X, Y and Z have the meanings described under formula I above. Compound (X) may be isolated or it can decarboxylate, sponatneously, or by heating in an inert solvent, such as DMSO to give a compound of formula (XI). Subsequent conversion to a compound of formuala ($I_{a03}$) can be achieved as described previously and shown in scheme 4. Alternatively, compound of formula (II) can be decarboxylatively cross-coupled with a compound of formula (XII) under very similar conditions to give a compound of formula (III). Conversion of compounds of formula (III) to compounds of formula ($I_{a01}$) have been previously described (scheme 1).

The Palladium cataylsed decarboxylative cross coupling has been described in analogous cases, e.g. in R. Shang et al. Angew. Chem. Int. Ed., 2011, 50, 4470.

Compounds of formula ($I_{a07}$) wherein, n is 1, p is 1, $R_1$ is H, $R_2$, $R_3$, $R_4$, $R_5$, $R_6$, X, Y, Z, $G_1$, $G_2$, V, and m are as described as in formula (I) can also be prepared as shown in scheme 5.

Scheme 5.

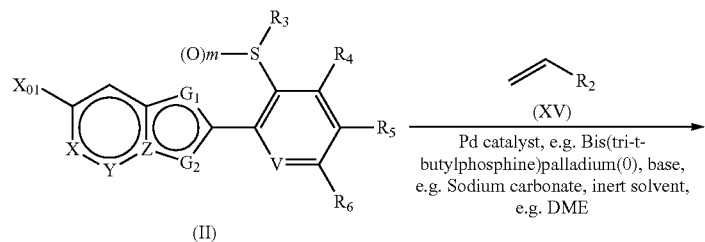
(II)

(XV)
Pd catalyst, e.g. Bis(tri-t-butylphosphine)palladium(0), base, e.g. Sodium carbonate, inert solvent, e.g. DME

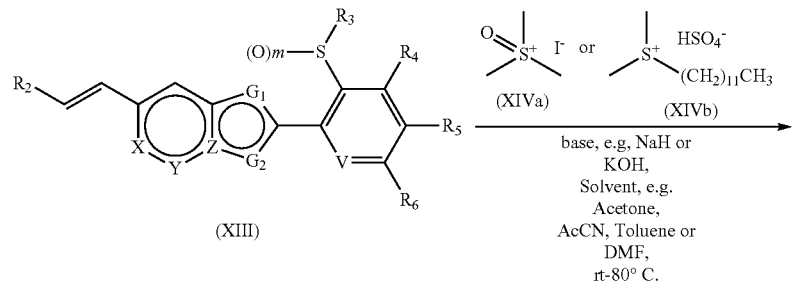
(XIII)

(XIVa) (XIVb)

base, e.g, NaH or KOH,
Solvent, e.g.
Acetone,
AcCN, Toluene or
DMF,
rt-80° C.

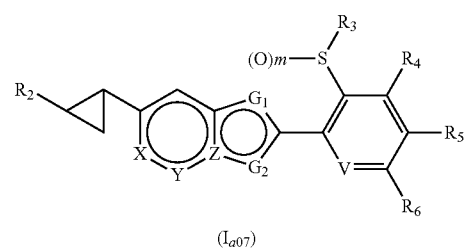
($I_{a07}$)

In scheme 6, compounds of formula (II) are reacted with compounds of formula (XV) under typical Heck conditions, for example those known to those skilled in the art and described for example in *Chem. Rev.* 2000, 100, 3009-3066. The compounds of formula (XIII) obtained can be treated with compounds of formula (XIVa) or (XIVb) and a base, for example an alkaline metal hydride, for example sodium hydride, or an alkali metal alkoxide, for example potassiumhydroxide, in an inert solvent such as DMF or toluene, to give compounds of formula ($I_{ao7}$) wherein $R_1$, X, Y, Z, $G_1$, $G_2$, V, $R_2$, $R_4$, $R_5$, $R_6$, $R_3$ and m have the meanings as defined for formula (I). Similar chemistry has been described in the literature, for example in *Tetrahedron*, Volume 43, Issue 12, 1987, Pages 2609-2651.

The required starting materials for preparation of compounds of formula (I), i.e compounds of formula (II) are in many cases known and described in the literature [Chemical abstract reference numbers]; 6-bromo-2-(3-ethylsulfanyl-2-pyridyl)-7-isopropyl-3-methyl-imidazo[4,5-b]pyridine [1421956-60-6], 6-bromo-7-(difluoromethyl)-2-(3-ethylsulfonyl-2-pyridyl)-3-methyl-imidazo[4,5-b]pyridine [1421956-59-3], 6-bromo-7-(difluoromethyl)-2-(3-ethylsulfinyl-2-pyridyl)-3-methyl-imidazo[4,5-b]pyridine [1421956-58-2], 6-bromo-7-(difluoromethyl)-2-(3-ethylsulfanyl-2-pyridyl)-3-methyl-imidazo[4,5-b]pyridine [1421956-57-1], 2-[3-ethylsulfonyl-5-(trifluoromethyl)-2-pyridyl]-6-iodo-3-methyl-imidazo[4,5-b]pyridine [1421956-26-4], 6-bromo-2-[3-ethylsulfonyl-5-(trifluoromethyl)-2-pyridyl]-3-methyl-imidazo[4,5-b]pyridine [1421956-07-1], 6-bromo-2-[3-ethylsulfinyl-5-(trifluoromethyl)-2-pyridyl]-3-methyl-imidazo [4,5-b]pyridine [1421956-06-0], 6-bromo-2-[3-ethylsulfanyl-5-(trifluoromethyl)-2-pyridyl]-3-methyl-imidazo[4,5-b]pyridine [1421956-04-8], 6-bromo-2-(3-ethylsulfanyl-2-pyridyl)-3-methyl-imidazo[4,5-b]pyridine-7-carbaldehyde [1421954-62-2], 6-bromo-2-(3-ethylsulfonyl-2-pyridyl)-3-methyl-imidazo[4,5-b]pyridine[1421954-25-7], 2-(3-ethylsulfonyl-2-pyridyl)-6-iodo-3-methyl-imidazo[4,5-b]pyridine[1421950-96-0], 2-[3-ethylsulfanyl-5-(trifluoromethyl)-2-pyridyl]-5-iodo-1-methyl-benzimidazole [1421950-48-2], 2-(3-ethylsulfanyl-2-pyridyl)-5-iodo-1-methyl-benzimidazole [1421950-16-4], 2-[3-ethylsulfanyl-5-(trifluoromethyl)-2-pyridyl]-5-iodo-1,3-benzoxazole [1616682-41-7], 2-[3-ethylsulfonyl-5-(trifluoromethyl)-2-pyridyl]-5-iodo-1,3-benzoxazole [1616682-43-9], 6-bromo-2-(5-bromo-3-ethylsulfonyl-2-pyridyl) oxazolo[5,4-b]pyridine [1616682-28-0], 6-bromo-2-[3-ethylsulfonyl-5-(trifluoromethyl)-2-pyridyl]oxazolo[5,4-b]pyridine [1616682-16-6], 5-bromo-2-[3-ethylsulfonyl-5-(trifluoromethyl)-2-pyridyl]-1,3-benzoxazole [1616682-19-9], 2-[3-ethylsulfanyl-5-(trifluoromethyl)-2-pyridyl]-6-iodo-thiazolo[5,4-b]pyridine [1421956-35-5], and 2-[2-ethylsulfanyl-4-(trifluoromethyl)phenyl]-6-iodo-thiazolo[5,4-b]pyridine [1383947-33-8].

Other Intermediates of formula (IIb),

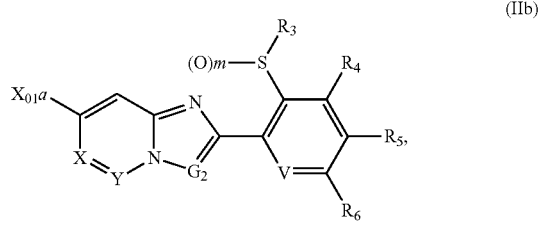

(IIb)

wherein $G_2$, $R_3$, $R_4$, $R_5$, $R_6$, m, V, X, and Y have the definitions as described above under formula (I), and $X_{01a}$ is halogen are novel and were developed specifically for the preparation of the compounds of the formula (I). Accordingly, they also form part of the subject-matter of the present invention.

The preferred substituent definitions for formula I, Ia, Ib, Ic and Id mentioned above are also valid for the preferred compounds of formula II.

Synthesis of the novel compounds of formula (IIb) wherein $G_2$, $R_3$, $R_4$, $R_5$, $R_6$, m, V, X, and Y, have the definitions as previously described, and $X_{01a}$ is halogen can be prepared by treatment of a compound of formula (XVI)

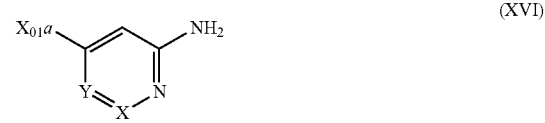

(XVI)

wherein Y, X, are as described in and $X_{01a}$ is halogen, with a compound of formula (XVII)

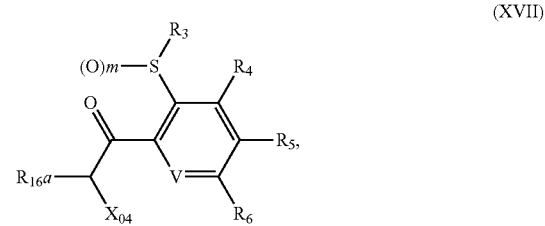

(XVII)

wherein $X_{04}$ is halogen, and $R_4$, $R_5$, $R_6$, $R_3$ and m have the definitions described for formula (I), and $R_{16}a$ is hydrogen or $C_1$-$C_4$alkyl, in an inert solvent optionally in the presence of a suitable base in an inert solvent, to give compounds of formula (IIba).

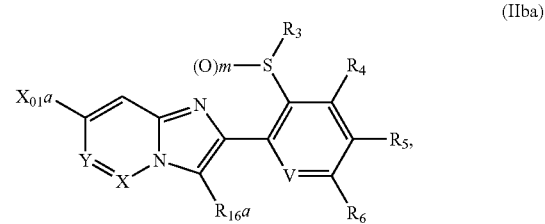

(IIba)

wherein Y, X, $X_{01a}$, V, $R_3$, $R_4$, $R_5$ and $R_6$ are as described in formula (I) and $R_{16}a$ is hydrogen or $C_1$-$C_4$alkyl. Such reactions are well precedented in the literature (for example see WO 2013191113, or *Archiv. Pharm. Res.*, 37(5), 588-599; 2014) and are usually carried out in an insert solvent such as ethanol or DMF at temperatures between 60-160° C., optionally in the presence of a base.

A further process to prepare compounds of formula (IIb), involves reacting a compound of formula (XIII) with a compound of (XVIII)

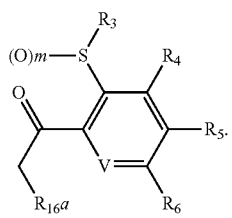

(XVIII)

In the presence of a Lewis acid, such as Zinc(II)iodide or Indium(III) triflate, in an inert solvent such as chlorobenzene or 1,2,dichlorobenzene, with a catalytic copper(II) salt, such as Cu(II)acetate, under an oxygen or air atmosphere at temperatures between 100-180° C., preferably 110-140° C., to give compounds of formula (IIba) wherein $R_{16a}$ is hydrogen. Such reactions have previously been described in the literature (see *Adv. Synth. Catal.* 2013, 355, 1741-1747, and *J. Org. Chem.,* 2013, 78, 12494-12504, when $R_{16a}$ is hydrogen). Compounds of formula (XVII) and (XVIII) can be prepared from compounds of formula (XIX) by, for example, the methods shown in scheme 6.

Scheme 6.

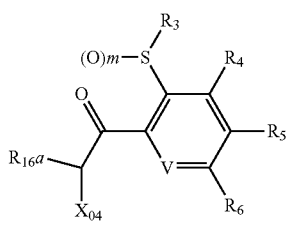

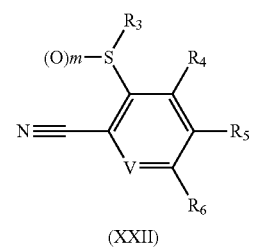

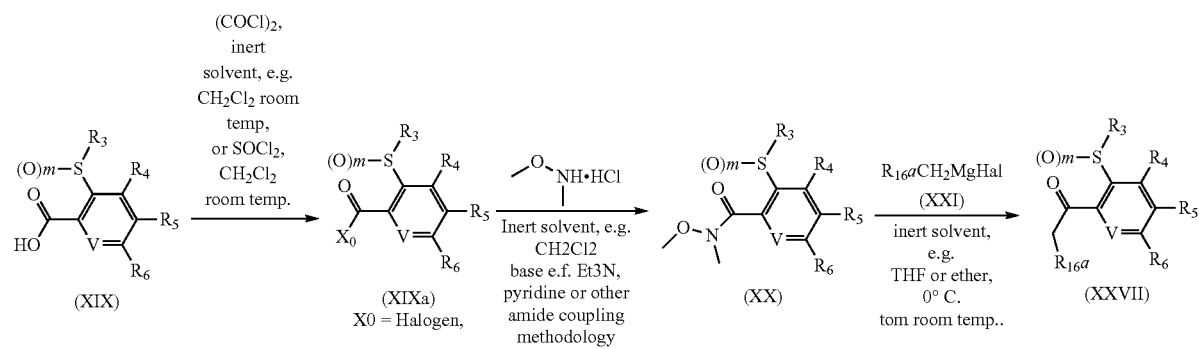

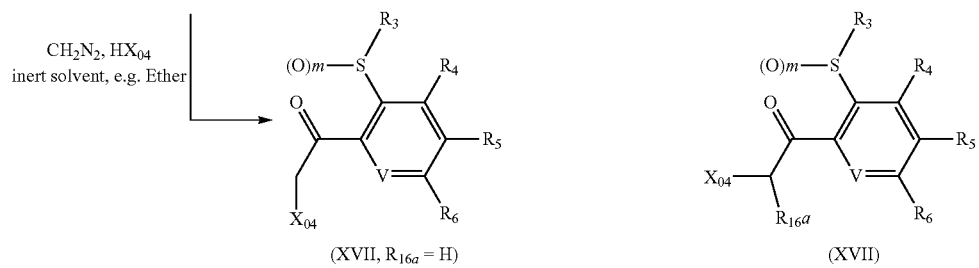

In scheme 6, an acyl halide of formula (XIXa) is converted to a Weinreb amide (XX) upon reaction with N,O-Dimethylhydroxylamine by methods known to those skilled in the art and described for example in C. Ferri, "Reaktionen der Organischen Synthese", Georg Thieme Verlag, Stuttgart, 1978, page 223ff. the Weinreb amide of formula (XX) is then reacted with a Grignard reagent of formula $R_{16a}CH_2MgHal$ (XXI) according to the method of Weinreb (*Tetrahedron Letters* 1981, 22, 3815-3818) to give compounds of formula XXVII and XXVIIa. Compounds of formula XXVII and XXVIIa can also be prepared by treatment of nitrile compounds of formula XXII, with a Grignard reagent of formula $R_{16a}CH_2MgHal$, followed by acidic hydrolysis (as described in C. Ferri, "Reaktionen der Organischen Synthese", Georg Thieme Verlag, Stuttgart, 1978, page 223ff.).

Compounds of formula XXVII and XXVIIa can be halogenated to compounds of formula XVII, with for example mixtures of bromine and hydrobromic acid in acetic acid (as described in *Phosphorus, Sulfur and Silicon and the Related Elements*, 2013, 188(12), 1835-1844) or with, for example, copper(II)bromide in an inert solvent, for example chloroform, ethyl acetate and the like, as described in *J. Med. Chem.*, 2013, 56(1), 84-96. Alternatively compounds of formula XVII where $R_{16a}$ is hydrogen, can be prepared directly from compounds of formula XIXa by treatment with diazomethane or trimethyl silyl diazomethane and subsequent treatment with an halogen acid, for example, hydrobromic acid or hydrochloric acid in an inert solvent such as diethyl ether. Such procedures are well known in the literature, for example see *Eu. J. Med. Chem.*, 1987, 22(5), 457-62 and WO 2009010455.

Compounds of the formula XVI are generally known in the literature, for example (CAS index numbers in brackets); 4-bromopyridin-2-amine [84249-14-9], 5-bromopyridazin-3-amine [1187237-00-8] and 6-bromopyrimidin-4-amine [1159818-57-1]. Compounds of formula (XIX) used in this invention are generally known and have been described in WO12/086848, WO13/018928, WO12/086848, WO 2013/187422, WO 2013/191113, and WO 2013/191188.

Compounds of formula (IIc)

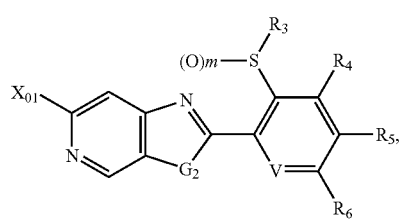

(IIc)

can be prepared for example as shown in scheme 7 for the representative example compound of formula (IIc$_{a01}$):

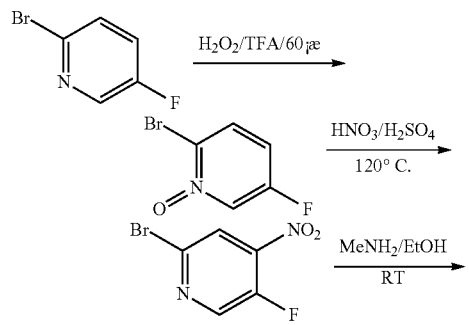

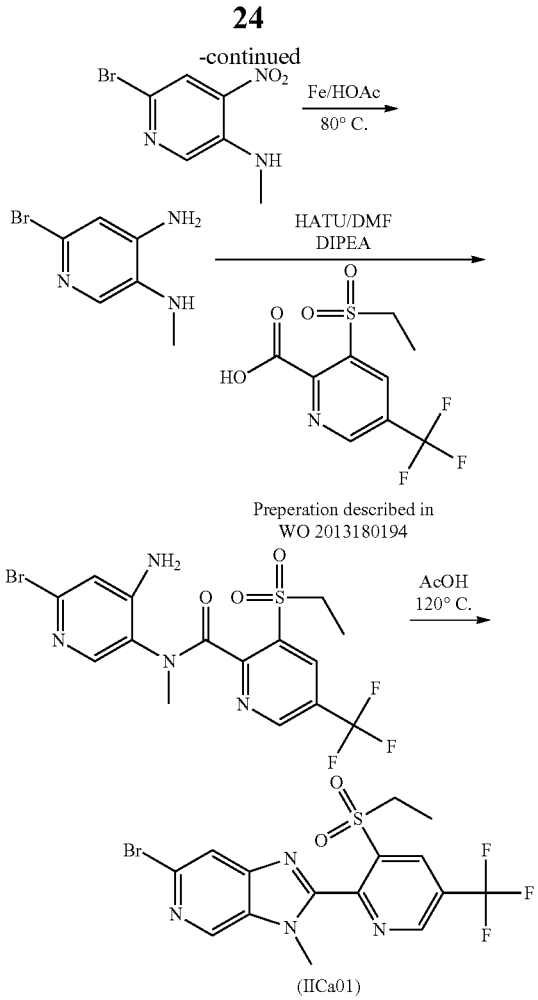

(IICa01)

Intermediates of formula (III),

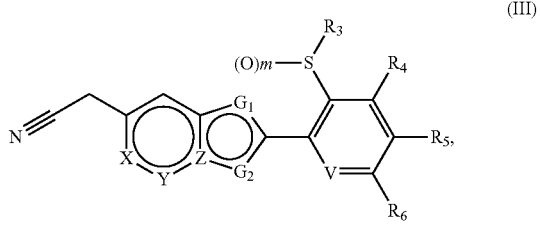

(III)

wherein $G_1$, $G_2$, $R_3$, $R_4$, $R_5$, $R_6$, m, V, X, Z and Y have the definitions as described under formula (I) above are novel and were developed specifically for the preparation of the compounds of the formula (I). Accordingly, they also form part of the subject-matter of the present invention. The preferred substituent definitions for formula I, Ia, Ib, Ic and Id mentioned above are also valid for the preferred compounds of formula III.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula (I) can be converted in a manner known per se into another compound of formula (I) by replacing one or more substituents of the starting compound of formula (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent.

Salts of compounds of formula (I) can be converted in the customary manner into the free compounds (I), acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I) I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

The compounds of formula (I) and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulphonic acid, for example camphorsulphonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 11 below can be prepared according to the methods described above. The examples which follow are intended to illustrate the invention and show preferred compounds of formula (I).

Table X: This table discloses the 27 substituent designations X.001 to X.027 for the formulae (Iaa), (Iab), (Iac).

(Iad), (Iae) and (Iaf) which are disclosed after Table X. In table X, Et represents $CH_2CH_3$, $CH_2Cyp$ represents

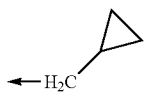

where the arrow represents the point of attachment to the sulphur.

TABLE X

| Comp. No | $R_1$ | $R_2$ | $R_3$ | $R_4$ | $R_5$ | $R_6$ | $R_{13}$ |
|---|---|---|---|---|---|---|---|
| X.001 | H | H | Et | H | $CF_3$ | H | H |
| X.002 | CN | H | Et | H | $CF_3$ | H | H |
| X.003 | H | H | Et | H | H | H | H |
| X.004 | CN | H | Et | H | H | H | H |
| X.005 | H | H | Et | H | $OCHF_2$ | H | H |
| X.006 | CN | H | Et | H | $OCHF_2$ | H | H |
| X.007 | H | CN | Et | H | $CF_3$ | H | H |
| X.008 | H | CN | Et | H | H | H | H |
| X.009 | H | H | $CH_2Cyp$ | H | $CF_3$ | H | H |
| X.010 | CN | H | $CH_2Cyp$ | H | $CF_3$ | H | H |
| X.011 | H | H | $CH_2Cyp$ | H | H | H | H |
| X.012 | CN | H | $CH_2Cyp$ | H | H | H | H |
| X.013 | H | H | $CH_2Cyp$ | H | $OCHF_2$ | H | H |
| X.014 | CN | H | $CH_2Cyp$ | H | $OCHF_2$ | H | H |
| X.015 | H | $CF_3$ | Et | H | $OCHF_2$ | H | H |
| X.016 | $CF_3$ | H | Et | H | $OCHF_2$ | H | H |
| X.017 | H | $CF_3$ | Et | H | $CF_3$ | H | H |
| X.018 | $CF_3$ | H | Et | H | $CF_3$ | H | H |
| X.019 | H | $CF_3$ | Et | H | H | H | H |
| X.020 | $CF_3$ | H | Et | H | H | H | H |
| X.021 | CN | H | Et | H | 4-(trifluoro-methyl)-phenyl | H | H |
| X.022 | CN | H | Et | H | 5-chloro 2-pyrimidyl | H | H |
| X.023 | CN | H | Et | H | 4-chloro-phenyl | H | H |
| X.024 | CN | H | Et | H | 2-pyrimidyl | H | H |
| X.025 | CN | H | Et | H | $CF_3$ | H | 4-(trifluoro-methyl)-2-pyridyl |
| X.026 | CN | H | Et | H | $CF_3$ | H | 5-(trifluoro-methyl)-3-pyridyl |
| X.027 | CN | H | Et | H | $CF_3$ | H | 2-(trifluoro-methyl)-4-pyridyl |

Table 1: This table discloses the 27 compounds 1.001 to 1.027 of the formula (Iaa):

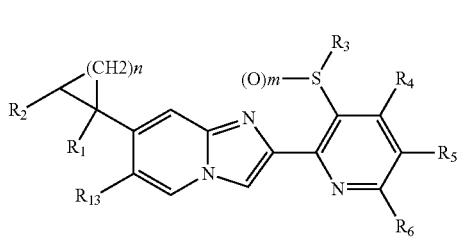

wherein n is 1, m is 2, and $R_1$, $R_2$, $R_3$, $R_4$, $R_5$, $R_6$ and $R_{13}$ are as defined in lines X.001-X.027 in table X. For example, compound 1.004 has the following structure:

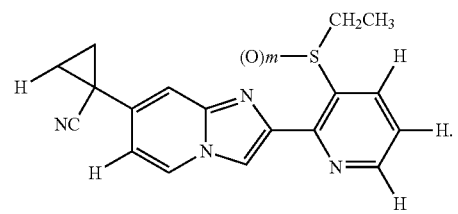

Table 2: This table discloses the 27 compounds 2.001 to 2.027 of the formula (Iab), wherein n is 1, m is 2, and $R_1$, $R_2$, $R_3$, $R_4$, $R_5$, $R_6$ and $R_{13}$ are as defined in lines X.001-X.027 of table X:

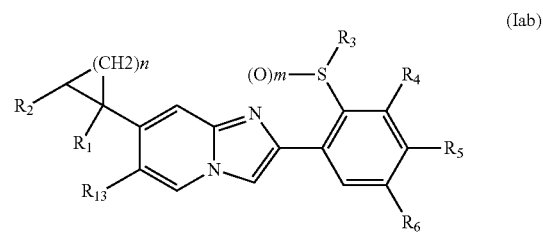

Table 3: This table discloses the 27 compounds 3.001 to 3.027 of the formula (Iac), wherein n is 1, m is 2, and $R_1$, $R_2$, $R_3$, $R_4$, $R_5$, $R_6$ and $R_{13}$ are as defined in lines X.001-X.027 of table X.

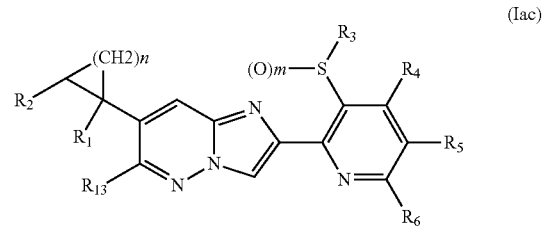

Table 4: This table discloses the 27 compounds 4.001 to 4.027 of the formula (Iad), wherein n is 1, m is 2, and $R_1$, $R_2$, $R_3$, $R_4$, $R_5$, $R_6$ and $R_{13}$ are as defined in lines X.001-X.027 of table X.

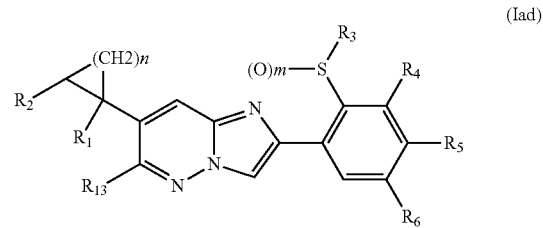

Table 5: This table discloses the 27 compounds 5.001 to 5.027 of the formula (Iae), wherein n is 1, m is 2, and $R_1$, $R_2$, $R_3$, $R_4$, $R_5$, $R_6$ and $R_{13}$ are as defined in lines X.001-X.027 of table X.

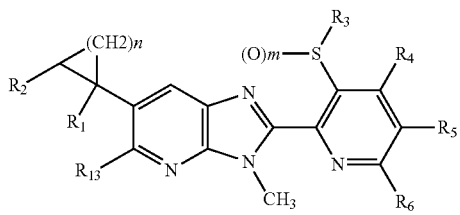

(Iae)

Table 6: This table discloses the 27 compounds 6.001 to 6.027 of the formula (Iaf), wherein n is 1, m is 2, and $R_1$, $R_2$, $R_3$, $R_4$, $R_5$, $R_6$ and $R_{13}$ are as defined in lines X.001-X.027 of table X.

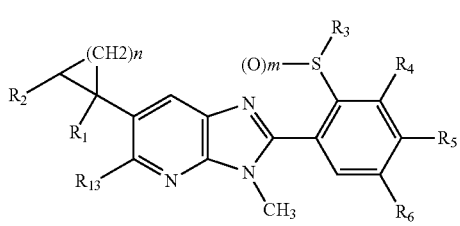

(Iaf)

Table 7: This table discloses the 27 compounds 7.001 to 7.027 of the formula (Iag), wherein n is 2, m is 2, and $R_1$, $R_2$, $R_3$, $R_4$, $R_5$, $R_6$ and $R_{13}$ are as defined in lines X.001-X.027 of table X.

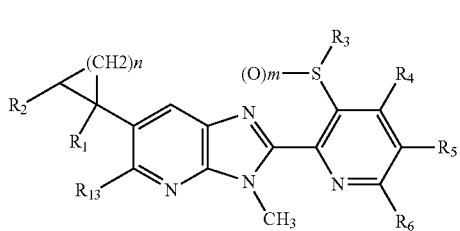

(Iag)

Table Y: This table discloses the 24 substituent designations Y.001 to Y.024 for the formulae (Iah), (Iai), (Iaj), and (Iak) which are disclosed after Table Y:

In table Y, Et represents $CH_2CH_3$, $CH_2Cyp$ represents

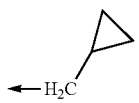

where the arrow represents the point of attachment to the sulphur.

TABLE Y

| Comp. No | $R_1$ | $R_2$ | $R_3$ | $R_4$ | $R_5$ | $R_6$ |
|---|---|---|---|---|---|---|
| Y.001 | H | H | Et | H | $CF_3$ | H |
| Y.002 | CN | H | Et | H | $CF_3$ | H |
| Y.003 | H | H | Et | H | H | H |
| Y.004 | CN | H | Et | H | H | H |
| Y.005 | H | H | Et | H | $OCHF_2$ | H |

TABLE Y-continued

| Comp. No | $R_1$ | $R_2$ | $R_3$ | $R_4$ | $R_5$ | $R_6$ |
|---|---|---|---|---|---|---|
| Y.006 | CN | H | Et | H | $OCHF_2$ | H |
| Y.007 | H | CN | Et | H | $CF_3$ | H |
| Y.008 | H | CN | Et | H | H | H |
| Y.009 | H | H | $CH_2Cyp$ | H | $CF_3$ | H |
| Y.010 | CN | H | $CH_2Cyp$ | H | $CF_3$ | H |
| Y.011 | H | H | $CH_2Cyp$ | H | H | H |
| Y.012 | CN | H | $CH_2Cyp$ | H | H | H |
| Y.013 | H | H | $CH_2Cyp$ | H | $OCHF_2$ | H |
| Y.014 | CN | H | $CH_2Cyp$ | H | $OCHF_2$ | H |
| Y.015 | H | $CF_3$ | Et | H | $OCHF_2$ | H |
| Y.016 | $CF_3$ | H | Et | H | $OCHF_2$ | H |
| Y.017 | H | $CF_3$ | Et | H | $CF_3$ | H |
| Y.018 | $CF_3$ | H | Et | H | $CF_3$ | H |
| Y.019 | H | $CF_3$ | Et | H | H | H |
| Y.020 | $CF_3$ | H | Et | H | H | H |
| Y.021 | CN | H | Et | H | 4-(trifluoromethyl)-phenyl | H |
| Y.022 | CN | H | Et | H | 5-chloro 2-pyrimidyl | H |
| Y.023 | CN | H | Et | H | 4-chlorophenyl | H |
| Y.024 | CN | H | Et | H | 2-pyrimidyl | H |

Table 8: This table discloses the 24 compounds 8.001 to 8.024 of the formula (Iah), wherein n is 1, m is 2, and $R_1$, $R_2$, $R_3$, $R_4$, $R_5$, and $R_6$ are as defined in lines Y.001-1.024 of table Y.

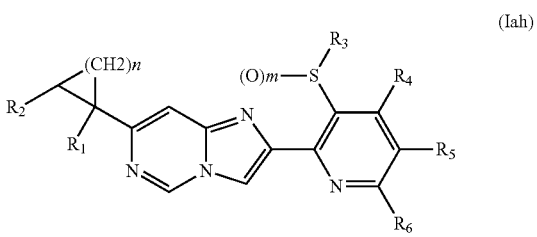

(Iah)

Table 9: This table discloses the 24 compounds 9.001 to 9.024 of the formula (Iai), wherein n is 1, m is 2, and $R_1$, $R_2$, $R_3$, $R_4$, $R_5$, and $R_6$ are as defined in lines Y.001-Y.024 of table Y.

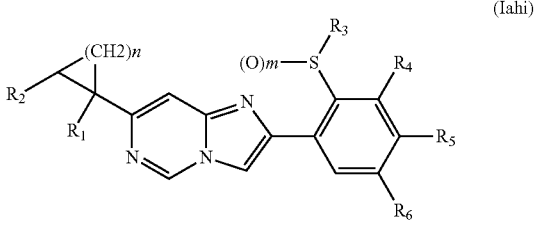

(Iahi)

Table 10: This table discloses the 24 compounds 10.001 to 10.024 of the formula (Iaj), wherein n is 1, m is 2, and $R_1$, $R_2$, $R_3$, $R_4$, $R_5$, and $R_6$ are as defined in lines Y.001-Y.024 of table Y.

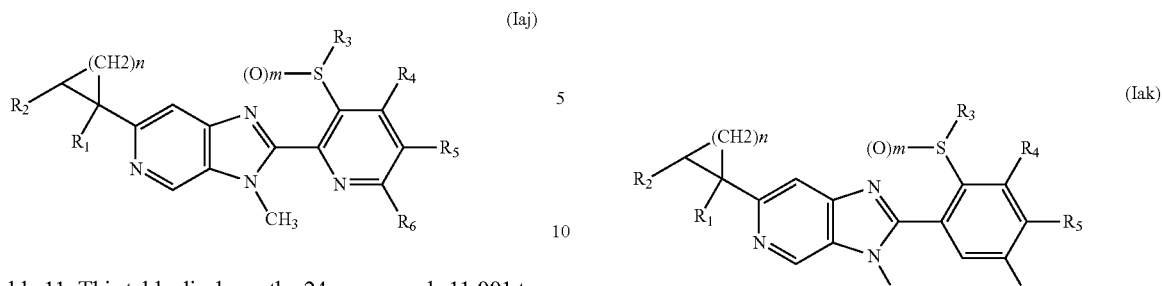
Table 11: This table discloses the 24 compounds 11.001 to 11.024 of the formula (Iak), wherein n is 1, m is 2, and $R_1$, $R_2$, $R_3$, $R_4$, $R_5$ and $R_6$ are as defined in lines Y.001-Y.024 of table Y.
TABLE A1
Physical Chemical Data of Prepared Compounds:
| Example | Compound | Ret. Time (min) | (M + H) Measured | Method | Mpt. ° C. |
|---|---|---|---|---|---|
| P1 | (Compound 5.001) | 1.01 | 411 | G | 99-100 |
| P2 | (Compound 5.002) | 0.94 | 436 | G | |
| P3 | (Compound 7.002) | 0.98 | 450 | G | |
| P4 | (Compound 5.007) | 0.89 | 436 | G | |

TABLE A1-continued
Physical Chemical Data of Prepared Compounds:
| Example | Compound | Ret. Time (min) | (M + H) Measured | Method | Mpt. ° C. |
|---|---|---|---|---|---|
| P5 | 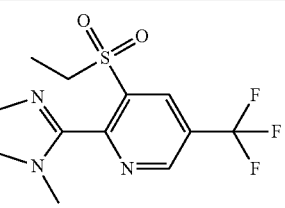 | 0.91 | 436 (M + H − CH3) | G | 224-225 |
| P6 | 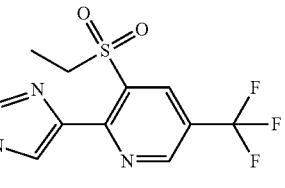<br>(Compound 10.002) | 0.68 | 411 | G | 179-180° C. |
TABLE B
Physical chemical data of prepared Intermediate compounds of formula (II) and formula (III).
| Entry No. | Compound | Ret. Time (min) | (M + H) Measured | Method | Mpt. ° C. |
|---|---|---|---|---|---|
| I-1 | 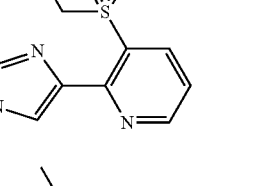 | 0.95 | 449/451 | G | 188-190° C. |
| I-2 | | 0.94 | 435/437 | G | — |
| I-3 | | 0.74 | 366/368 | G | 189-190° C. |
| I-4 | 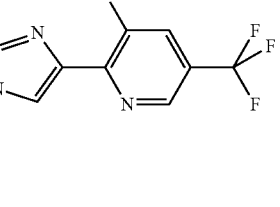 | 0.99 | 402/404 | G | |

TABLE B-continued

Physical chemical data of prepared Intermediate compounds of formula (II) and formula (III).

| Entry No. | Compound | Ret. Time (min) | (M + H) Measured | Method | Mpt. °C |
|---|---|---|---|---|---|
| I-5 | | 0.99 | 434/436 | G | 187-188° C. |
| I-6 | | 0.84 | 395 | G | 229-230° C. |
| I-7 | | 0.81 | 410 | G | 169-170° C. |

The compounds of formula I according to the invention are preventively and/or curatively valuable active ingredients in the field of pest control, even at low rates of application, which have a very favorable biocidel spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:
from the order Acarina, for example,

*Acalitus* spp, *Aculus* spp, *Acaricalus* spp, *Aceria* spp, *Acarus siro*, *Amblyomma* spp., *Argas* spp., *Boophi-lus* spp., *Brevipalpus* spp., *Bryobia* spp, *Calipitrimerus* spp., *Chori-optes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order Coleoptera, for example, *Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus subtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp., *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotino-phara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp,

*Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;*
from the order Hymenoptera, for example,
*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;
from the order Isoptera, for example,
*Coptotermes* spp, *Corniternes cumulans, Incisitermes* spp, *Macrotermes* spp, *Mastotermes* spp, *Microtermes* spp, *Reticulitermes* spp.; Solenopsis geminate
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;
from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Neocurtilla hexadactyla, Periplaneta* spp., *Scapteriscus* spp, *and Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis;*
from the order Thysanoptera, for example,
*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;
from the order Thysanura, for example, *Lepisma saccharine.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, *Cinnamonium* or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca*(preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belono*

*laimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, *Ampullariidae; Arion* (*A. ater, A. circumscriptus, A. hortensis, A. rufus*); *Bradybaenidae* (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); *Helicidae Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example Fusarium, Anthracnose, or Phytophthora), bacterial (for example Pseudomonas) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF—YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains am effective amount of a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/064072, WO 2006/128870, EP 1724392, WO 2005/113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
|  | *X. mutilatus* | Hardwoods |
|  | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
|  | *Agrilus politus* | Willow, Maple |
|  | *Agrilus sayi* | Bayberry, Sweetfern |
|  | *Agrilus vittaticolllis* | Apple, Pear, Cranberry, Serviceberry, Hawthorn |
|  | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
|  | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
|  | *Goes tigrinus* | Oak |
|  | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | *Neoptychodes trilineatus* | Fig, Alder, Mulberry, Willow, Netleaf hackberry |
|  | *Oberea ocellata* | Sumac, Apple, Peach, Plum, Pear, Currant, Blackberry |
|  | *Oberea tripunctata* | Dogwood, Viburnum, Elm, Sourwood, Blueberry, Rhododendron, Azalea, Laurel, Poplar, Willow, Mulberry |
|  | *Oncideres cingulata* | Hickory, Pecan, Persimmon, Elm, Sourwood, Basswood, Honeylocust, Dogwood, Eucalyptus, Oak, Hackberry, Maple, Fruit trees |
|  | *Saperda calcarata* | Poplar |
|  | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
|  | *Dendroctonus frontalis* | Pine |
|  | *Dryocoetes betulae* | Birch, Sweetgum, Wild cherry, Beech, Pear |
|  | *Monarthrum fasciatum* | Oak, Maple, Birch, Chestnut, Sweetgum, Blackgum, Poplar, Hickory, Mimosa, Apple, Peach, Pine |
|  | *Phloeotribus liminaris* | Peach, Cherry, Plum, Black cherry, Elm, Mulberry, Mountain-ash |
|  | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
|  | *Sannina uroceriformis* | Persimmon |
|  | *Synanthedon exitiosa* | Peach, Plum, Nectarine, Cherry, Apricot, Almond, Black cherry |
|  | *Synanthedon pictipes* | Peach, Plum, Cherry, Beach, Black Cherry |
|  | *Synanthedon rubrofascia* | Tupelo |
|  | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
|  | *Vitacea polistiformis* | Grape |

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
active ingredient: 1 to 95%, preferably 5 to 20%
surfactant: 1 to 30%, preferably 10 to 20
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

"M.p." means melting point in ° C. Free radicals represent methyl groups.
LCMS Methods:
Method G—Standard:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=acetonitrile+0.05% HCOOH: gradient: gradient: 0 min 0% B, 100% A; 1.2-1.5 min 100% B; flow (ml/min) 0.85

Method H—Standard Long:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=acetonitrile+0.05% HCOOH: gradient: gradient: 0 min 0% B, 100% A; 2.7-3.0 min 100% B; flow (ml/min) 0.85

Method I—Unpolar:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=acetonitrile+0.05% HCOOH: gradient: gradient: 0 min 40% B, 60% A; 1.2-1.5 min 100% B; flow (ml/min) 0.85

Mass Spectroscopy Method MS

LC-20AD Mass Spectrometer from Shimadzu (Single Quadrupole Mass Spectrometer)

Instrument Parameters:

Ionisation method: Electrospray

Polarity: positive and negative ions

Capillary (kV) 1.50

Cone (V) unknown

Extractor (V) 5.00

Source Temperature (° C.) 200

Desolvation Temperature (° C.) 250

Cone gas Flow (l/Hr) 90

Desolvation gas Flow (l/Hr) 90

Mass range: 50 to 1000 Da

Example P1: 1-[2-[3-ethylsulfonyl-5-(trifluoromethyl)-2-pyridyl]-3-methyl-imidazo[4,5-b]pyridin-6-yl]cyclopropanecarbonitrile (Compound 5.002)

(Compound 5.002)

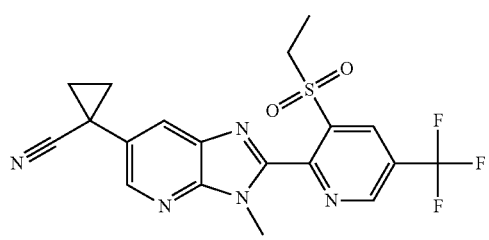

Step A: 2-[2-[3-ethylsulfonyl-5-(trifluoromethyl)-2-pyridyl]-3-methyl-imidazo[4,5-b]pyridin-6-yl]acetonitrile

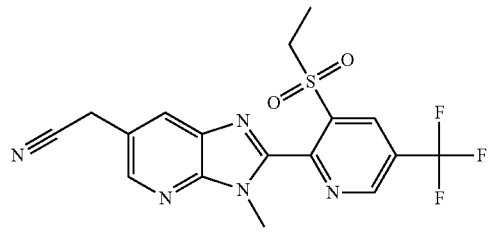 [SMILES: CCS(=O)(=O)c1cc(C(F)(F)F)cnc1-c1nc2cc(CC#N)cnc2n1C]

To a 2-5 mL microwave vial containing 2.2 ml of DMF was added tris(dibenzylideneacetone)dipalladium(0) (11 mg, 0.011 mmol), Zinc(II)fluoride (69 mg, 0.67 mmol) 4,5-bis(diphenylphosphino)-9,9-dimethylxanthene (Xantphos, 13 mg, 0.022 mmol), 2-trimethylsilylacetonitrile (150 mg, 1.3 mmol)), and 6-bromo-2-[3-ethylsulfonyl-5-(trifluoromethyl)-2-pyridyl]-3-methyl-imidazo[4,5-b]pyridine (500 mg, 1.1 mmol, prepared as described in WO 2013018928). The cap was sealed and the mixture heated to 140° C. for 30 min in the microwave. LCMS analysis after this time showed reaction completion. The mixture was cooled and diluted with ter-butyl methyl ether, washed with water and then brine, and the organixc layer dried over anhydrous Na2SO4, filtered and concentrated in vacuo. The crude brown residue was purified over a silica gel cartridge (Rf200) eluting with cyclohexane/ethyl acetate to give the title product as a beige powder.

HPLC 0.87 (method G), 0.87 mins (MH+(410)).

$^1$H NMR (400 MHz, chloroform-d) δ ppm; 1.45 (t, J=7.34 Hz, 3H); 3.94 (s, 3H); 3.97-4.05 (m, 4H); 8.16 (d, J=2.20 Hz, 1H) 8.49 (d, J=2.20 Hz, 1H) 8.81 (d, J=1.83 Hz, 1H) 9.27 (d, J=2.20 Hz, 1H).

Step B: 1-[2-[3-ethylsulfonyl-5-(trifluoromethyl)-2-pyridyl]-3-methyl-imidazo[4,5-b]pyridin-6-yl]cyclopropanecarbonitrile (Compound 5.002)

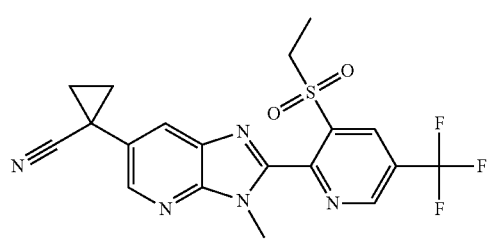 [SMILES: CCS(=O)(=O)c1cc(C(F)(F)F)cnc1-c1nc2cc(C3(C#N)CC3)cnc2n1C]

To a solution 2-[2-[3-ethylsulfonyl-5-(trifluoromethyl)-2-pyridyl]-3-methyl-imidazo[4,5-b]pyridin-6-yl]acetonitrile (300 mg, 0.73 mmol) in acetonitrile (10 ml) was added cesium carbonate (720 mg, 2.20 mmol) and 1,2 dibromoethane (280 mg, 1.50 mmol). The brown solution was stirred at ambient temperature for 1 hour and then heated to 70° C. LC/MS showed formation of desired product after 1 hour. The reaction was cooled and allowed to stir at ambient temperature for a further 4 days, and then diluted with ethyl acetate and water, the organic layer separated, and washed successively with water and brine, dried over Na2SO4, filtered and concentrated in vacuo. The crude mixture was purified over a silica gel cartridge (Rf200) eluting with Cychexane/Ethyl acetate to give the title compound as a yellow resin.

LCMS (Method G) Rt. 0.94 min, 436 (M+H). ¹H NMR (400 MHz, chloroform-d) 5 ppm 1.44 (t, J=7.52 Hz, 3H); 1.52-1.57 (m, 2H); 1.70 (br. s., 1H); 1.83-1.89 (m, 2H); 4.01 (q, J=7.46 Hz, 2H); 8.08 (d, J=2.20 Hz, 1H); 8.56 (d, J=1.83 Hz, 1H); 8.80 (d, J=1.83 Hz, 1H); 9.26 (d, J=1.10 Hz, 1H).

Example P2: 1-[2-[3-ethylsulfonyl-5-(trifluoromethyl)-2-pyridyl]-3-methyl-imidazo[4,5-b]pyridin-6-yl]cyclobutanecarbonitrile (Compound No. 7.002)

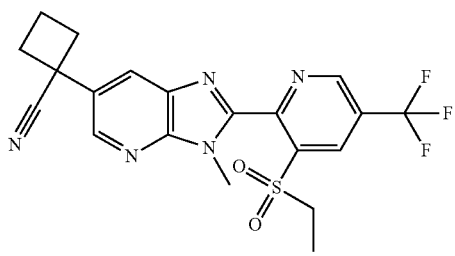

(Compound 7.002)

A solution of 2-[2-[3-ethylsulfonyl-5-(trifluoromethyl)-2-pyridyl]-3-methyl-imidazo[4,5-b]pyridin-6-yl]acetonitrile (prepared as in Step A example P1, 200 mg, 0.49 mmol) were dissolved in dimethylformamide and cooled to 0° C., under argon. To this solution were added sodium hydride (47 mg, 55% in mineral oil therefore 25 mg, 1.1 mmol) and the reaction mixture was stirred at 0° C. for 30 min and then treated with 1,3-dibromopropane (200 mg, 0.98 mmol). The brown reaction mixture was stirred under ice-bath-cooling-.for 1 Hr and then allowed to warm to ambient temperature and stirred for 18 hours. The mixture was quenched with saturated aqueous NH4Cl (exothermic, temperature increase to 35° C.) and extracted with tert-butyl methyl ether (×3). The combined organic layers were washed successively with water and brine, dried over Na₂SO₄, filtered and concentrated in vacuo. The crude product was Purified over silica gel cartridge (Rf200) eluting with cyclohexane/ethyl acetate to give the title compound as a colourless resin.

LCMS (Method G); Rt=0.98 min, (M+H) 450. ¹H NMR (400 MHz, Chloroform-d) δ ppm: 1.42 (t, J=7.34 Hz, 3H); 2.12-2.25 (m, 1H); 2.45-2.62 (m, 1H); 2.69-2.81 (m, 2H); 2.90-3.07 (m, 2H); 3.95 (s, 3H); 4.00 (q, J=7.34 Hz, 2H); 8.11 (d, J=2.20 Hz, 1H); 8.61 (d, J=2.20 Hz, 1H); 8.78 (d, J=2.20 Hz, 1H) 9.24 (dd, J=2.20, 0.73 Hz, 1H).

Example P3. 2-[2-[3-ethylsulfonyl-5-(trifluoromethyl)-2-pyridyl]-3-methyl-imidazo[4,5-b]pyridin-6-yl]cyclopropanecarbonitrile. (Compound No. 5.007)

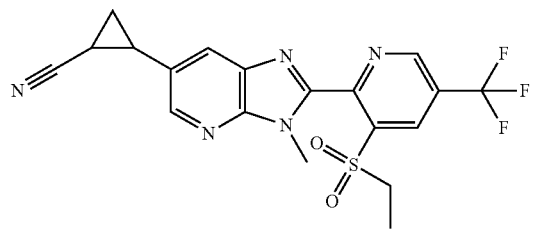 [SMILES: CCS(=O)(=O)c1cc(C(F)(F)F)cnc1-c1nc2cc(C3CC3C#N)cnc2n1C]

(Compound No. 5.007)

Step A: (E,Z)-3-[2-[3-ethylsulfonyl-5-(trifluoromethyl)-2-pyridyl]-3-methyl-imidazo[4,5-b]pyridin-6-yl]prop-2-enenitrile (E)-3-[2-[3-ethylsulfonyl-5-(trifluoromethyl)-2-pyridyl]-3-methyl-imidazo[4,5-b]pyridin-6-yl]prop-2-enenitrile (0.5 g, 1.1 mmol) was dissolved in DMF (1.5 ml) and treated with acrylonitrile (240 mg, 4.5 mmol). The reaction was flushed with argon and then N-ethyl-N-isopropyl-propan-2-amine, tri(o-tolyl)phosphine (62 mg, 0.2 mmol) and palladium(II)acetate (23 mg, 0.1 mmol) were added. The brown solution was stirred over night at 120° C.

After 14 hours the same quantities of palladium(II)acetate and tri(o-tolyl)phosphine were added again and the mixture was stirred at 120° C. for a further 14 hr. After this time the reaction mixture was allowed to cool down to ambient temperature and diluted with ethyl acetate and water. The organic layer was separated, washed again with water and once with brine, dried over Na2SO4, filtered and concentrated in vacuo. The crude product was purified over a silica gel cartridge (Rf200). Eluting with cyclohexane:ethyl acetate, to give the title compound as a beige solid (3:1 E/Z isomer mixture).

LCMS (Method G); Rt=0.93 min, (M+H) 422.

Step B: 2-[2-[3-ethylsulfonyl-5-(trifluoromethyl)-2-pyridyl]-3-methyl-imidazo[4,5-b]pyridin-6-yl]cyclopropanecarbonitrile. (Example 5.007)

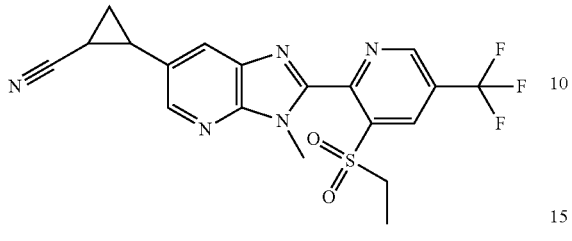

Trimethylsulfoxonium iodide (760 mg, 3.3 mmol) was suspended in 4 ml DMSO and treated with sodium hydride (130 mg of a 55% suspension in mineral oil, therefore 71 mg, 3.0 mmol). The mixture was stirred was stirred for 45 min at rt, and then 2-[2-[3-ethylsulfonyl-5-(trifluoromethyl)-2-pyridyl]-3-methyl-imidazo[4,5-b]pyridin-6-yl]acetonitrile (280 mg, 0.66 mmol) in 3 ml DMSO and added slowly to the suspension. The resulting red solution was stirred at rt. LC/MS analysis after 2 hr detected desired mass at 0.69 min and starting material at 0.94 min. The reaction mixture was allowed to stir overnight and then quenched with aqueous saturated $NH_4Cl$ and extracted with EtOAc (×3). The combined organic layers were washed once with brine, dried over Na2SO4, filtered and concentrated in vacuo. The crude reaction mixture was purified over a silica gel cartridge ($R_f$200) eluting with Cyclohexane/EtOAc to give two products which were further purified by reverse phase chromatography. This gave as a the first eluting compound the title compound:

LCMS (Method G); Rt=0.89 min, (M+H) 436, Rt=0.89. $^1$H NMR (400 MHz, chloroform-d) δ ppm: 1.40 (t, J=7.34 Hz, 3H); 1.61-1.72 (m, 2H); 1.98 (td, J=8.44, 5.87 Hz, 1H); 2.69-2.78 (m, 1H); 3.92 (s, 3H); 3.93-4.10 (m, 2H); 7.97 (d, J=1.47 Hz, 1H); 8.54 (d, J=2.20 Hz, 1H); 8.77 (d, J=1.47 Hz, 1H); 9.22 (d, J=1.47 Hz, 1H);

A second product was eluted which was identified as 2-[2-[3-ethylsulfonyl-5-(trifluoromethyl)-2-pyridyl]-3-methyl-imidazo[4,5-b]pyridin-6-yl]-1-methyl-cyclopropanecarbonitrile (Compound P5 table A1):

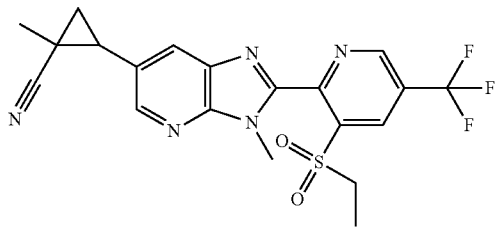 [SMILES: CCS(=O)(=O)c1cc(C(F)(F)F)cnc1-c1nc2cc(C3CC3(C)C#N)cnc2n1C]

LCMS (Method G); R.t=0.91 min, (M+H)—CH3, 436. $^1$H NMR (400 MHz, chloroform-d) δ ppm 1.40 (t, J=7.52 Hz, 3H) 1.53-1.61 (m, 3H) 1.63-1.70 (m, 1H) 1.76 (dt, J=9.35, 5.41 Hz, 1H) 3.89 (s, 3H) 3.97 (q, J=7.34 Hz, 2H) 7.75-7.80 (m, 1H) 8.42 (d, J=1.83 Hz, 1H) 8.77 (d, J=2.20 Hz, 1H) 9.19-9.26 (m, 1H).

Example P4: 6-cyclopropyl-2-[3-ethylsulfonyl-5-(trifluoromethyl)-2-pyridyl]-3-methyl-imidazo[4,5-b]pyridine (Compound 5.001)

(Compound 5.001)

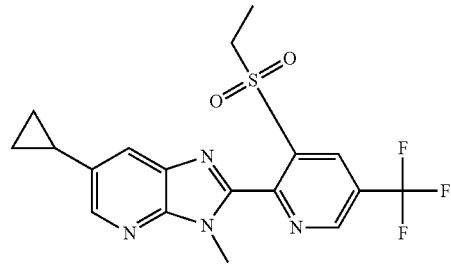

6-bromo-2-[3-ethylsulfonyl-5-(trifluoromethyl)-2-pyridyl]-3-methyl-imidazo[4,5-b]pyridine (500 mg, 1.1 mmol, prepared as described in WO 2013/018928), potassium cyclopropyltrifluoroborate (300 mg, 2.2 mmol), Bis(tri-t-butylphosphine)palladium(O) (23 mg, 0.045 mmol) and sodium carbonate (170 mg, 1.6 mmol)) were dissolved in dimethoxy ethane. The reaction mixture was transferred to a microwave vial and heated at 140° C. for 80 min.

The reaction mixture was then allowed to cool and diluted with water and ethyl acetate. The organic layer was separated, washed with water and brine, dried over $Na_2SO_4$, filtered and concentrated in vacuo. The crude product was dissolved in dichloromethane and put on adsorbed on teflon bulk sorbents, which was then purified over silica gel cartridge (Rf200) eluting with cyclohexane/ethyl acetate, and then by preparative RP HPLC, to give the title compound as a white solid.

LCMS (Method G); R.t=1.01 min, (M+H), 411; 1H NMR (400 MHz, chloroform-d) δ ppm 0.67-0.73 (m, 2H) 0.96-1.02 (m, 2H) 1.32 (t, J=7.34 Hz, 3H) 2.01 (tt, J=8.48, 5.09 Hz, 1H) 3.81 (s, 3H) 3.93 (q, J=7.46 Hz, 2H) 7.61 (d, J=1.83 Hz, 1H) 8.32 (d, J=1.83 Hz, 1H) 8.67-8.69 (m, 1H) 9.13 (dd, J=2.20, 0.73 Hz, 1H).

Intermediate I-1: 6-bromo-2-[3-ethylsulfonyl-5-(trifluoromethyl)-2-pyridyl]-3-methyl-imidazo[4,5-c]pyridine

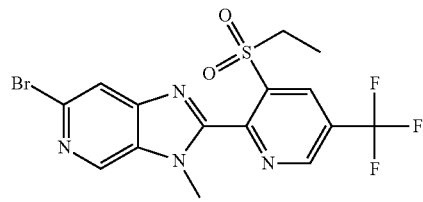 [SMILES: CCS(=O)(=O)c1cc(C(F)(F)F)cnc1-c1nc2cc(Br)ncc2n1C]

Step A: 2-bromo-5-fluoro-1-oxido-pyridin-1-ium

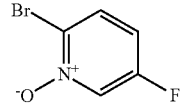

To a stirred solution of 2-bromo-5-fluoropyridine (50.0 g, 0.284 mol) in TFA (100.0 mL) was added H$_2$O$_2$ (30%, 150 mL) dropwise at 0° C. and the mixture stirred at 60-70° C. overnight. After cooling, the reaction mixture was poured onto ice-water, extracted with dichloromethane/methanol (10:1, 500 mL×3), the organic layer was washed with saturated sodium bicarbonate solution and brine, and dried over anhydrous sodium sulfate. After filtration and concentration in vacuo, the crude product (off white solid) was used for the next step without further purification.

Step B: 2-bromo-5-fluoro-4-nitro-pyridine

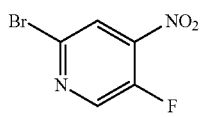

To a solution of 2-bromo-5-fluoro-1-oxido-pyridin-1-ium (46 g, 0.239 mmol) in sulphuric acid (conc., 200 mL) was added fuming nitric acid (100 mL) slowly at 0° C. After the addition, the reaction temperature was raised to 120° C., and stirring continued at this temperature for 8 h. After cooling to ambient temperature, the reaction solution was poured onto ice-water. The pH value was adjusted to 1 with NH$_4$OH, extracted with ethyl acetate (400 mL×3), the organic layer was washed with saturated sodium bicarbonate solution and brine, and dried over anhydrous sodium sulfate. After filtration and concentration in vacuo, the crude product was purified by column chromatography to afford the title compound as light yellow solid.

Step C: 6-bromo-N-methyl-4-nitro-pyridine-3-amine

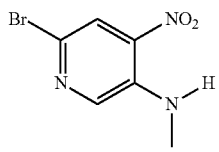

To a solution of 2-bromo-5-fluoro-4-nitropyridine (15 g, 67.8 mmol) in ethanol (100 mL) was added 30% MeNH$_2$/ethanol (60 mL). The reaction mixture was stirred at ambient temperature for 4 hr. The mixture was then concentrated in vacuo to give the title compound as a solid which was used for the next step without further purification.

Step D: 6-bromo-N3-methyl-pyridine-3,4-diamine: (Method A)

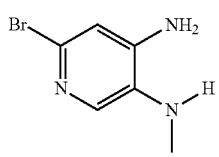

To a solution of 6-bromo-N-methyl-4-nitro-pyridin-3-amine (14.9 g, 64.2 mmol) in methanol (150 mL) was added Raney Ni (20% wt), and then hydrazine hydrate (25 mL) was added dropwise at 0° C. The reaction mixture was stirred at ambient temperature for 1 hr. The Raney Ni was filtered off through celite; the filtrate was concentrated in vacuo and purified by chromatography column on silica gel (eluting with dichloromethane:methanol, 10:1) to afford the title compound as off-white solid. $^1$H NMR (400 MHz, DMSO-d$_6$): δ(ppm) 7.20 (s, 1H), 6.53 (s, 1H), 5.76 (brs, 2H), 4.81 (q, 1H), 2.70 (d, J=6.4 Hz, 3H). ESI-MS(+): 203 (M+H).

(Method B)

To a solution of 6-bromo-N-methyl-4-nitro-pyridin-3-amine (20 g, 86 mmol) in acetic acid (400 mL) was added Fe powder (24 g, 428 mmol) at ambient temperature. The reaction mixture was stirred at 80° C. for 5 h. The solid was filtered off through celite; the filtrate was adjusted to pH=4-5 by using aq. NaOH and then extracted with ethyl acetate. The organic layer was dried over anhydrous MgSO$_4$, filtered, and concentrated in vacuo. The residue was recrystallized from ethyl acetate to afford the title compound as off-white solid. $^1$H NMR (400 MHz, DMSO-d$_6$): δ(ppm) 7.20 (s, 1H), 6.53 (s, 1H), 5.76 (brs, 2H), 4.81 (q, 1H), 2.70 (d, J=6.4 Hz, 3H). ESI-MS(+): 203 (M+H).

Step F: N-(4-amino-6-bromo-3-pyridyl)-3-ethylsulfonyl-N-methyl-5-(trifluoromethyl)pyridine-2-carboxamide

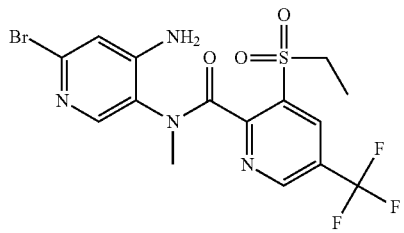 [SMILES: CCS(=O)(=O)c1cc(C(F)(F)F)cnc1C(=O)N(C)c1cnc(Br)cc1N]

To a stirred solution of 6-bromo-N3-methyl-pyridine-3,4-diamine (0.60 g, 2.96 mmol), 3-ethylsulfonyl-5-(trifluoromethyl)pyridine-2-carboxylic acid (0.92 g, 3.26 mmol, prepared as in WO 2013180194) and HATU (1.4 g, 3.68 mmol) in DMF (5.0 mL) was added DIPEA (1.2 ml, 7.26 mmol). The system was stirred at ambient temperature overnight. The reaction was diluted with EtOAc and H$_2$O, the organic layer was washed with brine and water, dried over anhydrous sodium sulfate. After filtration and concentration in vacuo, the crude title product was used for the next step without further purification.

Step G: 6-bromo-2-[3-ethylsulfonyl-5-(trifluoromethyl)-2-pyridyl]-3-methyl-imidazo[4,5-c]pyridine (Compound I-1)

(Compound I-1)

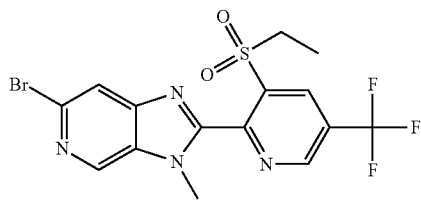

A solution of N-(4-amino-6-bromo-3-pyridyl)-3-ethylsulfonyl-N-methyl-5-(trifluoromethyl)pyridine-2-carboxamide (crude, 2.96 mmol) in acetic acid (5.0 mL) was stirred at 120° C. overnight. The mixture was evaporated to dryness. The residue was purified by chromatography on silica gel (Petroleum ether: EtOAc=4:1) to afford the title compound as white solid. $^1$H NMR (400 MHz, DMSO-$d_6$): δ (ppm) 9.53 (s, 1H), 8.94 (s, 1H), 8.74 (s, 1H), 8.01 (s, 1H), 3.83 (q, J=7.6 Hz, 2H), 3.79 (s, 3H), 1.19 (t, J=7.2 Hz, 3H). $^{19}$F NMR (300 MHz, DMSO-d6): δ (ppm) −60.42 (s, 3F). ESI-MS(+): 449 (M+H), 472 (M+Na); ESI-MS(−): 447 (M−H). Mpt. 188-190° C. LCMS (method SQD13): Rt. 0.95 min, 449/451 (M+H).

Formulation Examples (%=Percent by Weight)

| Example F1: Emulsion concentrates | | | |
|---|---|---|---|
| | a) | b) | c) |
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | | | | |
|---|---|---|---|---|
| | a) | b) | c) | d) |
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | | | | |
|---|---|---|---|---|
| | a) | b) | c) | d) |
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | | |
|---|---|---|
| | a) | b) |
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | | | |
|---|---|---|---|
| | a) | b) | c) |
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

| Example F6: Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

| Example F7: Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

| Example F8: Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Example F9: Powders for dry seed treatment

|  | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

Example F10: Emulsifiable concentrate

| | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Example F11: Flowable concentrate for seed treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and Bacillus thuringiensis preparations.

The following mixtures of the compounds of formula I with active ingredients are preferred (the abbreviation "TX" means "one compound selected from the group consisting of the compounds described in Table 1 to 11 and A of the present invention"):

an adjuvant selected from the group of substances consisting of petroleum oils (alternative name) (628)+TX,
an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeforrn hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion—S (1037)+TX, demeton (1038)+TX, demeton-methyl (224)+TX, demeton-O (1038)+TX, demeton-O-methyl (224)+TX, demeton—S (1038)+TX, demeton—S-methyl (224)+TX, demeton—S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dino-penton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin 1 (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, S1-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chlysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8-+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056),+TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion—S (1037)+TX, demeton (1038)+TX, demeton-methyl (224)+TX, demeton-O (1038)+TX, demeton-O-methyl (224)+TX, Demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name)

(473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nomicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, ometoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, S1-0205 (compound code)+TX, S1-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+

187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CON]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorphacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesamolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-

71-4]+TX, imazalil [35554-44-0]+TX, imiben-conazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethylpethyl]phenyl]-1H-pyrazole-4-carboxamide [926914-55-8]+TX, flufiprole [704886-18-0]+TX, cyclaniliprole [1031756-98-5]+TX, tetraniliprole [1229654-66-3]+TX, guadipyr (described in WO2010/060231)+TX and cycloxaprid (described in WO 2005/077934)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "*Compendium of Pesticide Common Names*", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula I selected from Table Table 1 to 11 and A with active ingredients described above comprises a compound selected from Table Table 1 to 11 and A and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Table Table 1 to 11 and A and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table Table 1 to 11 and A and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

The compounds (P1-P6) are shown in table A1.

Example B1: *Bemisia tabaci* (Cotton White Fly): Feeding/Contact Activity

Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compound resulted in at least 80% mortality at an application rate of 200 ppm: P2.

Example B2: *Diabrotica balteata* (Corn Root Worm): Feeding/Contact Activity Maize sprouts, placed on an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds resulted in at least 80% mortality at an application rate of 200 ppm: P6, P3, P1 and P2.

Example B3: *Euschistus heros* (Neotropical Brown Stink Bug): Feeding/Contact Activity Soybean leaf on agar in 24-well microtiter plates were sprayed with aqueous test solutions prepared from 10'000 ppm DMSO stock solutions. After drying the leaf were infested with N-2 nymphs. The samples were assessed for growth inhibition in comparison to untreated samples 5 days after infestation.

The following compound gave an effect of at least 80% in at least one of the two categories (mortality or growth inhibition) at an application rate of 200 ppm: P6.

Example B4: *Frankliniella occidentalis* (Western Flower *Thrips*): Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation. The following compound resulted in at least 80% mortality at an application rate of 200 ppm: P2

Example B5: *Myzus persicae* (Green Peach Aphid): Feeding/Contact Activity

Sunflower leaf discs were placed on agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P6, P1 and P2.

Example B6: *Myzus persicae* (Green Peach Aphid): Systemic Activity

Roots of pea seedlings infested with an aphid population of mixed ages were placed directly in the aqueous test solutions prepared from 10'000 ppm DMSO stock solutions. The samples were assessed for mortality 6 days after placing seedlings in test solutions.

The following compounds resulted in at least 80% mortality at a test rate of 24 ppm: P6 and P2.

Example B7: *Myzus persicae* (Green Peach Aphid): Intrinsic Activity

Test compounds from 10'000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm: P1 and P2.

Example B8: *Plutella xylostella* (Diamond Back Moth): Feeding/Contact Activity 24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: P6, P1 and P2

Example B9: *Spodoptera littoralis* (Egyptian Cotton Leaf Worm): Feeding/Contact Activity Cotton leaf discs were placed on agar in 24-well microtiter plates and sprayed with aqueous test solutions prepared from 10'000 ppm DMSO stock solutions. After drying the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample.

The following compounds resulted in at least 80% control at an application rate of 200 ppm: P6, P5, P1 and P2.

Example B10: *Spodoptera littoralis* (Egyptian Cotton Leaf Worm): Systemic Activity Test compounds were applied by pipette from 10'000 ppm DMSO stock solutions into 24-well plates and mixed with agar. Lettuce seeds were placed on the agar and the multi well plate was closed by another plate which contains also agar. After 7 days the roots have absorbed the compound and the lettuce has grown into the lid plate. The lettuce leafs were now cut off into the lid plate. *Spodoptera* eggs were pipetted through a plastic stencil on a humid gel blotting paper and the plate closed with it. The samples were assessed for mortality, anti-feedant effect and growth inhibition in comparison to untreated samples 6 days after infestation.

The following compounds gave an effect of at least 80% in at least one of the three categories (mortality, anti-feedancy, or growth inhibition) at a test rate of 12.5 ppm: P6 and P2.

Example B11: *Tetranychus urticae* (Two-Spotted Spider Mite):Feeding/Contact Activity Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compound resulted in at least 80% mortality at an application rate of 200 ppm: P4

Example B12: *Aedes aegypti* (Yellow Fever Mosquito): Feeding Contact Activity 10 to 15 *Aedes* larvae (L2) together with a nutrition mixture were placed in 96-well microtiter plates. Test compounds were pipetted into the wells. After an incubation period of 2 days insects were assessed for mortality and growth inhibition.

The following compound gave an effect of at least 80% in at least one of the two categories (mortality or growth inhibition) at a test rate of 5 ppm: P2.

The invention claimed is:
1. A compound of formula (I),

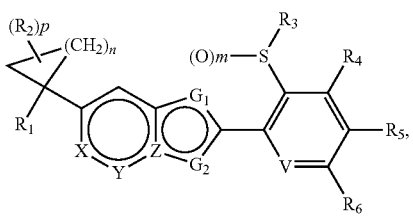

(I)

wherein
$R_1$ and $R_2$ are, independently from each other, hydrogen, $C_1$-$C_6$alkyl, $C_1$-$C_6$haloalkyl, cyano, nitro, $C(O)R_8$, $C(O)OR_9$, $CONR_{10}R_{11}$, or $S(O)_{m1}R_{12}$;
$R_3$ is $C_1$-$C_3$alkyl, $C_1$-$C_3$haloalkyl, $C_3$-$C_6$halocycloalkyl, $C_3$-$C_6$cycloalkyl-$C_1$-$C_4$alkyl, $C_3$-$C_5$ cycloalkyl or $C_3$-$C_6$halocycloalkyl-$C_1$-$C_4$alkyl;
$R_4$ and $R_6$ are hydrogen, halogen, or $C_1$-$C_3$alkyl;
$R_5$ is hydrogen, halogen, cyano, nitro, $C_1$-$C_4$alkoxy, $C_1$-$C_4$alkyl, or $C_1$-$C_4$alkyl mono- or polysubstituted by substituents selected from the group consisting of halogen, hydroxy, $C_1$-$C_4$haloalkoxy, $C_1$-$C_4$alkoxy and cyano; or is $C_3$-$C_6$cycloalkyl, or $C_3$-$C_6$cycloalkyl mono- or polysubstituted by substituents selected from the group consisting of $C_1$-$C_4$alkyl, and halogen; or
$R_5$ is $C_2$-$C_6$alkenyl, $C_2$-$C_6$haloalkenyl, $C_2$-$C_6$alkynyl, $C_2$-$C_6$haloalkynyl; or
$R_5$ is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and $C(O)C_1$-$C_4$haloalkyl; or
$R_5$ is $C_1$-$C_4$haloalkylsulfanyl, $C_1$-$C_4$haloalkylsulfinyl, $C_1$-$C_4$haloalkylsulfonyl, pentafluorosulfanyl, $C_1$-$C_4$haloalkoxy, $C(O)C_1$-$C_4$alkyl, $C_1$-$C_4$alkylsulfanyl, $C_1$-$C_4$alkylsulfinyl, or $C_1$-$C_4$alkylsulfonyl; or
X is $CR_{13}$;
Y is nitrogen;
$G_1$ is nitrogen;
V is nitrogen;
Z is carbon and $G_2$ is N—$R_7$;
$R_7$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl;
$R_5$, $R_9$, $R_{10}$, $R_{11}$, and $R_{12}$ independently of one another are hydrogen, $C_1$-$C_6$alkyl, $C_1$-$C_6$haloalkyl, $C_3$-$C_6$cycloalkyl, $C_3$-$C_6$halocycloalkyl or $C_1$-$C_6$alkoxy-$C_1$-$C_6$alkyl, with the proviso that when $m_1$ is 2, $R_{12}$ is different from hydrogen;
$R_{12}$ is hydrogen, halogen, $C_1$-$C_4$alkyl, $C_1$-$C_4$haloalkyl, $C_1$-$C_4$haloalkyl substituted by one or more methoxy groups, or $R_{13}$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy, phenylcarbonylsulfanyl, cyano, mercapto, or $C_1$-$C_4$alkoxycarbonyl;
n is 1 or 2;
m is 0, 1 or 2;
$m_1$ is 0, 1 or 2; and
p is 1, 2, 3 or 4;
or an agrochemically acceptable salt or N-oxide thereof.
2. The compound of claim 1, represented by the compound of formula (Ia)

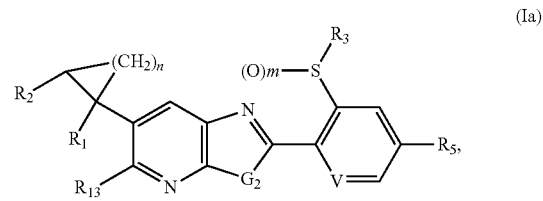

(Ia)

wherein;
$R_1$, $R_2$, $R_3$, $R_5$, $R_{13}$, V, n, and m are as defined under formula (I) in claim 1 and $G_2$ is nitrogen substituted with hydrogen or with $C_1$-$C_2$alkyl.
3. The compound of claim 1, wherein
$R_1$ is hydrogen or cyano;
$R_2$ is hydrogen;
$R_3$ is $C_1$-$C_4$alkyl;
$R_4$ is hydrogen;
$R_5$ is $C_1$-$C_4$haloalkyl;
$R_6$ is hydrogen;
p is 1;
n is 1 or 2;
m is 0 or 2;
X is CH;
Y is N;
Z is carbon;
$G_1$ is N;
$G_2$ is N—$R_7$;
$R_7$ is $C_1$-$C_4$alkyl; and
V is N.
4. A pesticidal composition, which comprises at least one compound of formula I according to claim 1 or a tautomer thereof, in each case in free form or in agrochemically utilizable salt form, as active ingredient and at least one auxiliary.
5. A method for controlling pests, which comprises applying a composition according to claim 4 to the pests or their environment with the exception of a method for treatment of the human or animal body by surgery or therapy and diagnostic methods practiced on the human or animal body.
6. A method for the protection of plant propagation material from the attack by pests, which comprises treating the propagation material or the site, where the propagation material is planted, with a composition according to claim 4.
7. The compound of claim 1, wherein $R_5$ is hydrogen, halogen, cyano, nitro, $C_1$-$C_4$alkoxy, $C_1$-$C_4$alkyl, or $C_1$-$C_4$alkyl mono- or polysubstituted by substituents selected from the group consisting of halogen, hydroxy, $C_1$-$C_4$haloalkoxy, $C_1$-$C_4$alkoxy and cyano; or is $C_3$-$C_6$cycloalkyl, or $C_3$-$C_6$cycloalkyl mono- or polysubstituted by substituents selected from the group consisting of $C_1$-$C_4$alkyl, and halogen.

8. The compound of claim 1, wherein $R_5$ is halogen, cyano, nitro, $C_1$-$C_4$alkoxy, $C_1$-$C_4$alkyl, or $C_1$-$C_4$alkyl mono- or polysubstituted by substituents selected from the group consisting of halogen, hydroxy, $C_1$-$C_4$haloalkoxy, $C_1$-$C_4$alkoxy and cyano; or is $C_3$-$C_6$cycloalkyl, or $C_3$-$C_6$cycloalkyl mono- or polysubstituted by substituents selected from the group consisting of $C_1$-$C_4$alkyl, and halogen.

9. The compound of claim 1, wherein $R_5$ is phenyl which can be mono- or polysubstituted by substituents selected from the group consisting of halogen, cyano, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkyl sulfonyl and —C(O)$C_1$-$C_4$haloalkyl; or $R_5$ is $C_1$-$C_4$haloalkylsulfanyl, $C_1$-$C_4$haloalkylsulfinyl, $C_1$-$C_4$haloalkylsulfonyl, pentafluorosulfanyl, $C_1$-$C_4$haloalkoxy, —C(O)$C_1$-$C_4$alkyl, $C_1$-$C_4$alkylsulfanyl, $C_1$-$C_4$alkylsulfinyl, or $C_1$-$C_4$alkylsulfonyl.

10. The compound of claim 1, wherein $R_5$ is $C_2$-$C_6$alkenyl, $C_2$-$C_6$haloalkenyl, $C_2$-$C_6$alkynyl, $C_2$-$C_6$haloalkynyl.

11. The compound of claim 3, wherein $R_5$ is trifluoromethyl.

12. The compound of claim 3, wherein $R_7$ is methyl.

13. The compound of claim 3, wherein m is 2.

14. The compound of claim 3, wherein $R_3$ is ethyl.

15. The method of claim 5, wherein the pest is an anthropod.

16. The method of claim 11, wherein the anthropod is an insect.

17. The method of claim 11, wherein the antropod is an acarina.

18. The method of claim 11, wherein the anthropod is selected from the group consisting of *Bemisia tabaci*, *Diabrotica balteata*, *Euschistus heros*, *Frankliniella occidentalis*, *Myzus persicae*, *Myzus persicae*, *Myzus persicae*, *Plutella xylostella*, *Spodoptera littoralis*, *Spodoptera littoralis*, *Tetranychus urticae*, and *Aedes aegypti*.

* * * * *